United States Patent
Picard et al.

(10) Patent No.: US 6,294,674 B1
(45) Date of Patent: Sep. 25, 2001

(54) DIBENZOFURAN SULFONAMIDE MATRIX METALLOPROTEINASE INHIBITORS

(75) Inventors: Joseph Armand Picard, Canton; Drago Robert Sliskovic, Saline, both of MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/254,403

(22) PCT Filed: Sep. 2, 1997

(86) PCT No.: PCT/US97/15444

§ 371 Date: Mar. 2, 1999

§ 102(e) Date: Mar. 2, 1999

(87) PCT Pub. No.: WO98/09957

PCT Pub. Date: Mar. 12, 1998

Related U.S. Application Data

(60) Provisional application No. 60/025,063, filed on Sep. 4, 1996, and provisional application No. 60/055,714, filed on Aug. 7, 1997.

(51) Int. Cl.[7] ............... C07D 307/91; C07D 405/12; C07D 409/12
(52) U.S. Cl. ............ 546/284.1; 548/195; 548/451; 548/454; 548/525; 549/60; 549/435; 549/460; 514/337; 514/371; 514/444; 514/468; 514/466; 514/414; 514/411; 514/422
(58) Field of Search ............... 549/60, 435, 460; 548/195, 451, 454, 525; 546/284.1; 514/468, 444, 337, 466, 414, 371, 411, 422

(56) References Cited

U.S. PATENT DOCUMENTS

| | | | |
|---|---|---|---|
| 3,845,097 | 10/1974 | Toyoshima et al. | 260/471 |
| 4,097,472 | 6/1978 | Okamoto et al. | 424/177 |
| 5,391,556 | * 2/1995 | Heckel et al. | 514/322 |
| 5,627,206 | 5/1997 | Hupe et al. | 514/468 |
| 5,665,764 | 9/1997 | Hupe et al. | 514/468 |

FOREIGN PATENT DOCUMENTS

| | | |
|---|---|---|
| 20 65 966 | 7/1977 | (DE) . |
| 0 183 271 | 5/1990 | (EP) . |
| 0 606 046 | 7/1994 | (EP) . |
| 96 38434 | 12/1996 | (WO) . |
| 97 19068 | 5/1997 | (WO) . |
| 97 27174 | 7/1997 | (WO) . |
| 98/09934 | 3/1998 | (WO) . |

OTHER PUBLICATIONS

Abdel–Ghaffar, et al. *J. Serb. Chem. Soc.*, Synthesis of Biologically Active Fluorene–2–Sulphonylamino Acid and Dipeptide Derivatives, vol. 55, No. 6, 1990, pp. 311–317.

El–Naggar, et al., *Acta Pharm. Jugosl.*, Synthesis and Biological Activity of Some New Dibenzofuran–and 7–Nitrodibenzofuran–2–Sulphonylamino Acid Derivatives, V–35, 1985, pp. 15–22.

* cited by examiner

Primary Examiner—Laura L. Stockton
(74) Attorney, Agent, or Firm—Charles W. Ashbrook

(57) ABSTRACT

The present invention relates to compounds of Formula I that inhibit matrix metalloproteinases and to a method of inhibiting matrix metalloproteinases using the compounds.

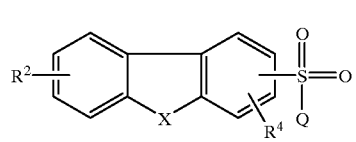

wherein Q is an un-natural amino acid. More particurlarly, the present invention relates to a method of treating diseases in which matrix metalloproteinases are involved such as multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

1 Claim, No Drawings

DIBENZOFURAN SULFONAMIDE MATRIX METALLOPROTEINASE INHIBITORS

This application is a 371 of PCT/US97/15444 filed Sep. 2, 1997 which claims the benefit of U.S. Provisional Application No. 60/025,063 filed Sep. 4, 1996 and U.S. Ser. No. 60/055,714 filed Aug. 7, 1997.

FIELD OF THE INVENTION

The present invention relates to compounds that inhibit matrix metalloproteinases and to a method of inhibiting matrix metalloproteinases using the compounds. More particularly, the present invention relates to a method of treating diseases in which matrix metalloproteinases are involved such as multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

BACKGROUND OF THE INVENTION

The compounds of the present invention are inhibitors of matrix metalloproteinases, e.g., stromelysin-1 and gelatinase A (72 kDa gelatinase).

Stromelysin-1 and gelatinase A are members of the matrix metalloproteinases (MMP). Other members include fibroblast collagenase, neutrophil collagenase, gelatinase B (92 kDa gelatinase), stromelysin-2, stromelysin-3, matrilysin, collagenase 3, and the newly discovered membrane-associated matrix metalloproteinases (Sato H., Takino T., Okada Y., Cao J., Shinagawa A., Yamamoto E., and Seiki M., *Nature*, 1994;370:61–65).

Stromelysin-1 is also known as MMP03 and gelatinase A is known as MMP02. In addition, several other matrix metalloproteinases are known:

MMP01—Fibroblast collagenase;

MMP07—Matrilysin;

MMP09Gelatinase B; and

MMP13—Collagenase -3.

The catalytic zinc in matrix metalloproteinases is typically the focal point for inhibitor design. The modification of substrates by introducing chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of atherosclerotic plaques is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galla Z. S., Sukhova G. K., Lark M. W., and Libby P., "Increased expression of matrix metalloproteinases and matrix degrading activity in vulnerable regions of human atherosclerotic plaques", *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases", *Clin. Sci.*, 1991;81:233–239).

Heart failure arises from a variety of diverse etiologies, but a common characteristic is cardiac dilation which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy", *Clin. Res.* 1993;41:660A; Tyagi S. C., Reddy H. K., Voelker D., Tjara I.E., and Weber K. T., "Myocardial collagenase in failing human heart", *Clin. Res.* 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction", *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure", *Am. J. Physiol.*, 1992;263:H266–H270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat", *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20 fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation", *Circulation Research*, 1994;75:41–54).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva", *J. Periodontal Res.*, 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva", *J. Periodontal Res.*, 1987;22:81–88). Proteolytic degradation of extracellular matrix has been observed in corneal ulceration following alkali bums (Brown S. I, Weller C. A., and Wasserman H. E., "Collagenolytic activity of alkali burned comeas", *Arch. Opthahnol.*, 1969;81:370–373). Thiol-containing peptides inhibit the collagenase isolated from alkali-burned rabbit corneas (Burns F. R., Stack M. S., Gray R. D., and Paterson C. A., *Invest. Opththamol.*, 1989;30:1569–1575).

Stromelysin is produced by basal keratinocytes in a variety of chronic ulcers (Saarialho-Kere U. K., Ulpu K., Pentland A. P., Birkedal-Hansen H., Parks W. C., Welgus H. G., "Distinct populations of basal keratinocytes express stromelysin-1 and stromelysin-2 in chronic wounds", *J. Clin. Invest.*, 1994;94:79–88).

Stromelysin-1 mRNA and protein were detected in basal keratinocytes adjacent to but distal from the wound edge in what probably represents the sites of proliferating epidermis. Stromelysin-1 may thus prevent the epidermis from healing.

Davies, et al., (*Cancer Res.*, 1993;53:2087–2091) reported that a peptide hydroxamate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.*, 1992;52:2353–2356), and the natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.*, 1992;52:701–708). Studies of human cancers have shown that gelatinase A is activated on the invasive tumor cell surface (Strongin A. Y., Mariner B. L., Grant G. A., and Goldberg G. I., *J. Biol. Chem.*, 1993;268:14033–14039) and is retained there through interaction with a receptor-like molecule (Monsky W. L., Kelly T., Lin C.-Y., Yeh Y., Stetler-Stevenson W.G., Mueller S.C., and Chen W.-T., *Cancer Res.*, 1993;53:3159–3164).

Inhibitors of MMPs have shown activity in models of tumor angiogenesis (Taraboletti G., Garofalo A., Belotti D., Drudis T., Borsotti P., Scanziani E., Brown P.D., and Giavazzi R., *Journal of the National Cancer Institute*, 1995;87:293; and Benelli R., Adatia R., Ensoli B., Stetler-Stevenson W. G., Santi L., and Albini A., *Oncology Research*, 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury", *Arthritis Rheum.*, 1992;35:3542; Zafarullah M., Pelletier J. P., Cloutier J. M., and Marcel-Pelletier J., "Elevated metalloproteinases and tissue inhibitor of metalloproteinase niRNA in human osteoarthritic synovia", *J. Rheumatol.*, 1993;20:693–697). TIMP-1 and TIMP-2 prevented the formation of collagen fragments, but not proteoglycan fragments, from the degradation of both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions*, 1992;37:147–154; Ellis A. J., Curry V. A., Powell E. K., and Cawston T. E., *Biochem. Bionhys. Res. Commun.*, 1994;201:94–101).

Gijbels, et al., (*J. Clin. Invest.*, 1994;94:2177–2182) recently described a peptide hydroxamate, GM6001, that suppressed the development or reversed the clinical expression of experimental allergic encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M. and Madri J. A., "The Induction of 72-kD Gelatinase in T Cells upon Adhesion to Endothelial Cells is VCAM-1 Dependent", *J. Cell Biology*, 1994; 125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provided the basis for the belief that an inhibitor of stromelysin-1 and/or gelatinase A will treat diseases involving disruption of extracellular matrix resulting in inflammation due to lymphocytic infiltration, inappropriate migration of metastatic or activated cells, or loss of structural integrity necessary for organ function.

We have identified a series of dibenzofuran sulfonamide compounds that are inhibitors of matrix metalloproteinases, particularly stromelysin-1 and gelatinase A, and thus usefull as agents for the treatment of multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

SUMMARY OF THE INVENTION

The present invention provides compounds of Formula I

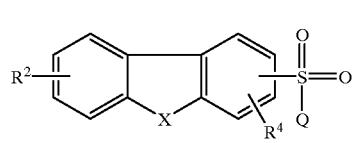

wherein Q is an un-natural amino acid;

X is O, S, S(O)$_n$, CH$_2$, CO, or NR$^{33}$;

R$^{33}$ is hydrogen, C$_1$–C$_6$ alkyl, or C$_1$–C$_6$ alkyl-phenyl;

R$^2$ and R$^4$ are independently hydrogen, C$_1$–C$_5$ alkyl, phenyl, —NO$_2$, halogen, —OR$^5$, —CN, —CO$_2$R$^5$, —SO$_3$R$^5$, —CHO, —COR$^5$, —CONR$^5$R$^6$, —(CH$_2$)$_n$NR$^5$R$^6$, —CF$_3$, or —NHCOR$^5$;

each R$^5$ and R$^6$ are independently hydrogen or C$_1$–C$_5$ alkyl; and n is 0 to 2, and the pharmaceutically acceptable salts, esters, amides, and prodrugs thereof.

In one embodiment of the invention, X is O
In another embodiment of the invention, X is S.
In another embodiment of the invention, X is $CH_2$.
In another embodiment of the invention, X is $NR^{33}$.
In another embodiment of the invention, $R^2$ and $R^4$ are hydrogen.
In another embodiment of the invention, X is CO.
In another embodiment of the invention, X is $S(O)_n$.
In another embodiment of the invention, Q is

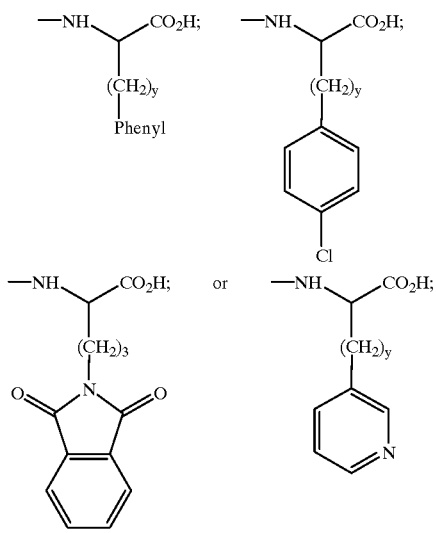

In a preferred embodiment, the present invention provides compounds having the Formula II

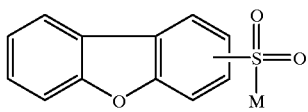

II wherein M is an un-natural amino acid,
and the pharnaceutically acceptable salts, esters, amides, and prodrugs thereof.
In a preferred embodiment, the un-natural amino acid is D-glycine, D-alanine, D-valine, D-leucine, D-isoleucine, D-phenylalanine, D-proline, D-serine, D-threonine, D-tyrosine, D-asparagine, D-glutamine, D-lysine, D-arginine, D-tryptophan, D-histidine, D-cysteine, D-methionine, D-aspartic acid, or D-glutamnic acid.
In a preferred embodiment the compound is:
(S)-3-[(dibenzofuran-2-sulfonylamino)-methyl]-5-methyl-hexanoic acid;
(S)-2-(dibenzofuran-2-sulfonylamino)-4-phenyl-butyric acid;
2-(Dibenzofuran-2-sulfonylamino)-5-phenyl-pentanoic acid;
2-(Dibenzofuran-2-sulfonylamino)-6-phenyl-hexanoic acid;
2-(Dibenzofuran-2-sulfonylamino)-7-phenyl-heptanoic acid;
4-(4-Chloro-phenyl)-2-(dibenzofuran-2-sulfonylamino)-butyric acid;
5-(4-Chloro-phenyl)-2-(dibenzofuran-2-sulfonylamino) pentanoic acid;
6-(4-Chloro-phenyl)-2-(dibenzofuran-2-sulfonylamino)-hexanoic acid;
7-(4-Chloro-phenyl)-2-(dibenzofuran-2-sulfonylamino)-heptanoic acid;
8-(4-Chloro-phenyl)-2-(dibenzofuran-2-sulfonylamino)-octanoic acid;
2-(Dibenzofuran-2-sulfonylamino)-4-(1,3-dioxo-1,3-dihydro-isoindol-2-yl)-butyric acid;
2-(Dibenzofuran-2-sulfonylamino)-5-(1,3-ioxo-1,3-dihydro-isoindol-2-yl)-pentanoic acid;
2-(Dibenzofuran-2-sulfonylamino)-4-(1,3-dioxo-1,3-dihydro-benzo[f]isoindol-2-yl)-butyric acid;
2-(Dibenzofuran-2-sulfonylamino)-5-(1,3-dioxo-1,3-dihydro-benzo[f]isoindol-2-yl)-pentanoic acid;
2(Dibenzofuran-2-sulfonylamino)-4-(1-oxo-1,3-dihydro-isoindol-2-yl)-butyric acid;
2-(Dibenzofuran-2-sulfonylamino-5-(1-oxo-1,3-dihydro-isoindol-2-yl)-pentanoic acid;
2-(Dibenzofuran-2-sulfonylamino)-5-(4-propyl-phenyl)-pentanoic acid;
2-(Dibenzofuran-2-sulfonylamino)-4-pyridin-3-yl-butyric acid;
2-(Dibenzofiuan-2-sulfonylamino)-5-pyridin-3-yl-pentanoic acid;
2-(Dibenzofuran-2-sulfonylamino)-succinic acid;
2-(Dibenzofuran-2-sulfonylamino)-pentanedioic acid;
2-(Dibenzofuran-2-sulfonylamino)hexanedioic acid;
2-(Dibenzofuran-2-sulfonylamino)succinic acid 4-methyl ester;
2-(Dibenzofuran-2-sulfonylamino)pentanedioic acid 5-methyl ester;
2-(Dibenzofuran-2-sulfonylamino)hexanedioic acid 6-methyl ester;
2-(Dibenzofuran-2-sulfonylamino)-3-(4-hydroxy-phenylsulfanyl)-propionic acid;
2-(Dibenzofuran-2-sulfonylamino)-pent-4-enoic acid;
2-[(Dibenzofuran-2-sulfonyl)methyl-amino]-5-phenyl-pentanoic acid;
5-(4-Chloro-phenyl)-2-[(dibenzofuran-2-sulfonyl)-methyl-amino]-pentanoic acid;
2-[(Dibenzofuran-2-sulfonyl)-methyl-amino]-5-(1,3-dioxo-1,3-dihydro-isoindol-2-yl)-pentanoic acid;
2-[(Dibenzofuran-2-sulfonyl)-phenethyl-amino]-5-phenyl-pentanoic acid;
2-[(Dibenzofuran-2-sulfonyl)-pyridin-3-yl-methyl-amino]-5-phenyl-pentanoic acid;
5-(4-Chloro-phenyl)-2-[(dibenzofuran-2-sulfonyl)-isobutyl-amino]-pentanoic acid;
2-[Benzyl-(dibenzofuran-2-sulfonyl)-amino]-5-(4-ethyl-phenyl)-pentanoic acid; and
2-[(Dibenzofuran-2-sulfonyl)-(2-phenoxy-ethyl)-amino]-pent-4-enoic acid.
Also provided is a method of inhibiting a matrix metalloproteinase in a patient in need of matrix metalloproteinase inhibition, the method comprising administering to the patient a therapeutically effective amount of a compound of Formula I or II.
Also provided is a method of treating multiple sclerosis, the method comprising administering to a patient having multiple sclerosis a therapeutically effective amount of a compound of Formula I or II.
Also provided is a method of treating atherosclerotic plaque rupture, the method comprising administering to a patient having an atherosclerotic plaque at risk for rupture a therapeutically effective amount of a compound of Formula I or II.

Also provided is a method of treating or preventing restenosis, the method comprising administering to a patient having restenosis or at risk of having restenosis a therapeutically effective amount of a compound of Formula I or II.

Also provided is a method of treating aortic aneurism, the method comprising administering to a patient having aortic aneurism a therapeutically effective amount of a compound of Formula I or II.

Also provided is a method of treating heart failure, the method comprising administering to a patient having heart failure a therapeutically effective amount of a compound of Formula I or II.

Also provided is a method of treating periodontal disease, the method comprising administering to a patient having periodontal disease a therapeutically effective amount of a compound of Formula I or II.

Also provided is a method of treating corneal ulceration, the method comprising administering to a patient having corneal ulceration a therapeutically effective amount of a compound of Formula I or II.

Also provided is a method of treating burns, the method comprising administering to a patient having burns a therapeutically effective amount of a compound of Formula I or II.

Also provided is a method of treating decubital ulcers, the method comprising administering to a patient having decubital ulcers a therapeutically effective amount of a compound of Formula I or II.

Also provided is a method of treating chronic ulcers or wounds, the *method comprising administering to a patient having chronic ulcers or wounds a therapeutically effective amount of a compound of Formula I or II.

Also provided is a method of treating cancer metastasis, the method comprising administering to a patient having cancer metastasis a therapeutically effective amount of a compound of Formula I or II.

Also provided is a method of treating tumor angiogenesis, the method comprising administering to a patient having tumor angiogenesis a therapeutically effective amount of a compound of Formula I or II.

Also provided is a method of treating arthritis, the method comprising administering to a patient having arthritis a therapeutically effective amount of a compound of Formula I or II.

Also provided is a method of treating autoimmune or inflammatory diseases dependent upon tissue invasion by leukocytes, the method comprising administering to a patient having autoimmune or inflammatory diseases dependent upon tissue invasion by leukocytes a therapeutically effective amount of a compound of Formula I or II.

In a preferred embodiment of the compounds of Formula I

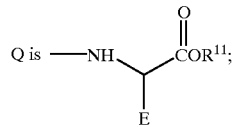

E is —$(CH_2)_m$—NH—Z—$R^{10}$,
—$(CH_2)_m$—S—C(phenyl)$_3$,
—$(CH_2)_m$—O—$(CH_2)_L$-phenyl,
—$(CH_2)_m$—O—$C_1$-$C_6$ alkyl,
$(CH_2)_m$-aryl,

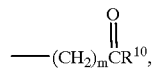

—$(CH_2)_m$ NHSO$_2$-aryl,
$C_1$-$C_6$ alkyl,
phenyl,
—$(CH_2)_m$-cycloalkyl,

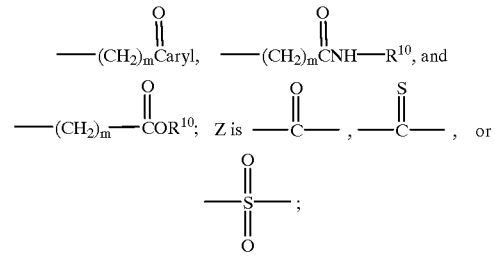

m is 1 to 6;
L is 1 to 6;
$R^{10}$ is —O$(CH_2)_m$-aryl,
—$(CR^{11}R^{12})_m$—S-aryl,
—$(CR^{11}R^{12})_m$—S-heteroaryl,
—$(CR^{11}R^{12})_m$—O-aryl,
—$(CR^{11}R^{12})_m$—O-heteroaryl,
—$(CR^{11}R^{12})_m$-ayl,
—$(CH_2)_m$—$C_2$-$C_8$ cycloalkenyl,
—$(CH_2)_m$-heteroaryl,

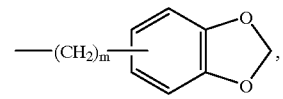

—NH—$C_2$-$C_8$ cycloalkyl,
—$(CH_2)_m$ NH-aryl,
—NH—$C_1$-$C_6$ alkenyl,
—NH-adamantyl

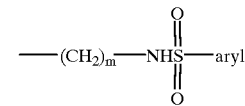

—$C_2$-$C_8$ cycloalkyl,
—$(CH_2)_m$—C(phenyl)$_3$,
—NH-aryl,
—NH$(CH_2)_m$-aryl,
—$(CH_2)_m$ NR$^{11}$R$^{12}$,
—NH-heteroaryl,
—NH—CH(phenyl)$_2$,
—$C_1$-$C_6$ alkenyl-phenyl,
—cycloalkyl-phenyl,

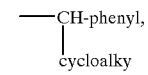

—O$C_1$-$C_6$ alkyl,
$C_1$-$C_6$ alkyl,
O-adamantyl,

O-$C_1$–$C_6$ alkenyl,
aryl,
heteroaryl, or
—$(CH_2)_m$—CH(phenyl)$_2$;
each $R^{11}$ and $R^{12}$ are independently hydrogen or $C_1$–$C_6$ alkyl.
In a more preferred embodiment, $R^{11}$ is hydrogen.
In another preferred embodiment,
E is —$(CH_2)_m$—NH—Z—$R^{10}$, and Z is 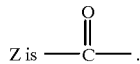

In another preferred embodiment,
E is —$(CH_2)_m$—NH—Z—$R^{10}$, and

Z is 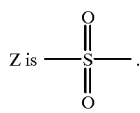

In a more preferred embodiment,
$R^{11}$ is hydrogen;
X is O;
$R^2$ and $R^4$ are hydrogen;
E is —$(CH_2)_m$—NH—Z—$R^{10}$; and Z is 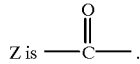

In a preferred embodiment,
$R^{10}$ is —O$(CH_2)_m$-phenyl, —$(CH_2)_m$—phenyl, —$(CH_2)_m$-heteroaryl, —$(CH_2)_m$—O-phenyl, —$(CH_2)_m$—O-heteroaryl, or —$(CH_2)_m$-naphthyl.
In a preferred embodiment,
$R^{10}$ is phenyl, heteroaryl, naphthyl, or $C_2$–$C_6$ alkenyl-phenyl.

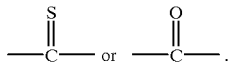

In a preferred embodiment, Z is
In a preferred embodiment,
$R^{10}$ is —NH-heteroaryl,
—NH—$(CH_2)_n$-phenyl,
—NH—$(CH_2)$-naphthyl,
—NH—adamantyl, or
—NH—$C_2$–$C_6$ alkenyl.
In a preferred embodiment,

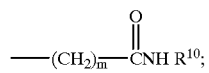

$R^{11}$ is hydrogen;
X is O; and
$R^2$ and $R^4$ are hydrogen.
In a preferred embodiment,
$R^{10}$ is —$(CH_2)_m$-heteroaryl,
$C_1$–$C_6$ alkyl,
phenyl,
—$(CH_2)_m$—NH($C_1$–$C_6$ alkyl),
—$(CH_2)_n$—N($C_1$–$C_6$ alkyl)$_2$, or
—$(CH_2)_m$-phenyl
In a most preferred embodiment, the present invention provides the compounds:

6-[2-(4-Chloro-phenoxy)-2-methyl-propionylamino]-2-(dibenzofuran-2-sulfonylamino)-hexanoic acid;

2-(Dibenzofuran-2-sulfonylamino)-6-[2-(pyridin-4-ylsulfanyl)-acetylamino]-hexanoic acid;

2-(Dibenzofuran-2-sulfonylamino)-6-[2-(2,4-dichloro-phenoxy)-acetylamino]-hexanoic acid;

2-(Dibenzofuran-2-sulfonylamino)-6-[2-(2-trifluoromethyl-phenyl)-acetylamino]-hexanoic acid;

2-(Dibenzofuran-2-sulfonylamino)-6-(2-thiophen-2-yl-acetylamino)-hexanoic acid;

2-(Dibenzofuran-2-sulfonylamino)-6-(2-phenoxy-butyrylamino)-hexanoic acid;

2-(Dibenzofuran-2-sulfonylamino)-6-(phenyisulfanyl-acetylamino)-hexanoic acid;

2-(Dibenzofuran-2-sulfonylamino)-6-(2-phenoxy-acetylamino)-hexanoic acid;

2-(Dibenzofuran-2-sulfonylamino)-6-[2-(3,4-dimethoxy-phenyl)-acetylamino]-hexanoic acid;

6-[2-(4-tert-Butyl-phenoxy)-acetylamino]-2-(dibenzofuran-2-sulfonylamino)-hexanoic acid;

2-(Dibenzofuran-2-sulfonylamino)-6-[3-(3,4-dimethoxy-phenyl)-propionylatnino]-hexanoic acid;

6-(2-(Cyclopent-1-enyl-acetylamino)-2(dibenzofuran-2-sulfonylamino)-hexanoic acid;

2-(Dibenzofuran-2-sulfonylamino)-6-[2-(4methoxy-phenoxy)-acetylamino]-hexanoic acid;

2-(Dibenzofuran-2-sulfonylamino)-6-[2-(naphthalen-1-yloxy)-acetylamino]-hexanoic acid;

2-(Dibenzofuran-2-sulfonylamino)-6-[2-(4nitro-phenoxy)-acetylamino]-hexanoic acid;

6-[4-(4-Chloro-3-methyl-phenoxy)-butyrylamino]-2-(dibenzofilran-2-sulfonylamino)-hexanoic acid;

2-(Dibenzofuran-2-sulfonylamino)-6-[3-(4-methoxy-phenyl)-propionylamino]-hexanoic acid;

2-(Dibenzofuran-2-sulfonylamino)-6-(2-pyridin-3-yl-acetylamino)-hexanoic acid;

6-(2-Benzo[1,3]dioxol-5-yl-acetylamino)-2-(dibenzofuran-2-sulfonylamino)-hexanoic acid;

2-(Dibenzofuran-2-sulfonylamino)-6-(2-pyridin-2-yl-acetylamino)-hexanoic acid;

2-(Dibenzofuran-2-sulfonylamino)-6-[4-(4-nitro-phenyl)-butyrylamino]-hexanoic acid;

2-(Dibenzofuran-2-sulfonylamino)-6-(3-pyridin-4-yl-propionylamino)-hexanoic acid;

2-(Dibenzofuran-2-sulfonylamino)-6-(2-phenylamino-acetylamino)-hexanoic acid;

2-(Dibenzofuran-2-sulfonylamino)-6-(2-indol-1-yl-acetylamino)-hexanoic acid;

2-(Dibenzofuran-2-sulfonylamino)-6-[3-(2-methoxy-phenyl)-propionylamino]-hexanoic acid;

2-(Dibenzofuran-2-sulfonylamino)-6-(4-phenyl-butyrylamino)-hexanoic acid;

2-(Dibenzofuran-2-sulfonylamino)-6-(3-p-tolyl-propionylamino)-hexanoic acid;

6-[3-(4-Chloro-phenyl)-propionylamino]-2-(dibenzofuran-2-sulfonylamino)-hexanoic acid;

6-[2-(2-Benzyloxy-phenyl)-acetylamino]-2-(dibenzofuran-2-sulfonylamino)-hexanoic acid;

2-(Dibenzofuran-2-sulfonylamino)-6-[2-naphthalen-2-yl-acetylamino)-hexanoic acid;

2-(Dibenzofuran-2-sulfonylamino)-6-(4-1H-indol-3-yl-butyrylamino)-hexanoic acid;

2-(Dibenzofuran-2-sulfonylamino)-6-(2-naphthalen-1-yl-acetylamino)-hexanoic acid;

6-[3-(4-Chloro-phenoxy)-propionylamino]-2-(cibenzofuran-2-sulfonylamino)-hexanoic acid;

2-(Dibenzofuran-2-sulfonylamino)-6-(6-phenyl-hexanoylamino)-hexanoic acid;

2-(Dibenzofuran-2-sulfonylamino)-6-[4-thiophen-2-yl-butyrylamino)-hexanoic acid;

2-(Dibenzofuran-2-sulfonylamino)-6-[3,3,3-triphenyl-propionylamino)-hexanoic acid;

2-(Dibenzofuran-2-sulfonylamino)-6-(3-diethylamino-propionylamino)-hexanoic acid;

2-(Dibenzofuran-2-sulfonylamino)-6-(1-phenyl-cyclopropane carbonylamino)-hexanoic acid;

6-(3-Benzo[1,3]dioxol-5-yl-propionylamino)-2-(dibenzofuran-2-sulfonylamino)-hexanoic acid;

6-[(Cyclopentyl-phenyl-acetyl)-amino]-2-(dibenzofuran-2-sulfonylamino)-hexanoic acid;

2-(Dibenzofuran-2-sulfonylamino)-6-[3-(4-methoxy-phenyl)-ureido]- hexanoic acid;

2-(Dibenzofuran-2-sulfonylamino)-6-[3-(3,4-dichloro-phenyl)-ureido]-hexanoic acid;

2-(Dibenzofuran-2-sulfonylamino)-6-(3-pyridin-3-yl-thioureido)hexanoic acid;

6-(3-Benzhydryl-thioureido)-2-(dibenzofuran-2-sulfonylamino)-hexanoic acid;

6-(3-Benzyl-thioureido)-2-(dibenzofuran-2-sulfonylamino)-hexanoic acid;

6-(3-Adamantan-1-yl-thioureido)-2-(dibenzofuran-2-sulfonylamino)-hexanoic acid;

2-(Dibenzofuran-2-sulfonylamino)-6-(3-naphthalen-2-yl-thioureido)-hexanoic acid;

6-(3-Allyl-ureido)-2-(dibenzofuran-2-sulfonylamino)-hexanoic acid;

6-(3-Benzy]-ureido)-2-(dibenzofinran-2-sulfonylamino)-hexanoic acid;

2-(Dibenzofuran-2-sulfonylamino)-6-(3-phenyl-ureido)-hexanoic acid;

2-(Dibenzofuran-2-sulfonylamino)-6-(3-phenyl-acryloylamino)-hexanoic acid;

2-(Dibenzofuran-2-sulfonylamino)-6-phenylacetylamino-hexanoic acid;

2-(Dibenzofuran-2-sulfonylamino)-6-(3-phenyl-propionylamino)-hexanoic acid;

6-[2-(4-Chloro-phenoxy)acetylamino]-2-(dibenzofuran-2-sulfonylamino)-hexanoic acid;

2-(Dibenzofuran-2-sulfonylamino)-6-[2-(2,4,6-triisopropyl-phenyl)-acetylamino]-hexanoic acid;

2-(Dibenzofuran-2-sulfonylamino)-6-(2-phenyl-butyrylamino)-hexanoic acid;

2-(Dibenzofuran-2-sulfonylamino)-6-(4-fluoro-benzenesulfonylamino)-hexanoic acid;

2-(Dibenzofuran-2-sulfonylamino)-6-(4-methoxy-benzenesulfonylamino)-hexanoic acid;

6-(4-Bromo-benzenesulfonylamino)-2-(dibenzofuran-2-sulfonylamino)-hexanoic acid;

6-(2-Acetylamino-thiazole-5-sulfonylamino)-2-(dibenzofuran-2-sulfonylamino)hexanoic acid;

6-(4-Acetylamino-benzensulfonylamino)-2-(dibenzofuran-2-sulfonylamino)-hexanoic acid;

6-Benzenesulfonylamino-2-(dibenzofuran-2-sulfonylamino)-hexanoic acid;

6-(Butane-1-sulfonylamino)-2-(dibenzofuran-2-sulfonylamino)-hexanoic acid;

2-(Dibenzofuran-2-sulfonyiamino)-6-(naphthalene-2-sulfonylamino)-hexanoic acid;

2-(Dibenzofuran-2-sulfonylamino)-6-(naphthalene-1-sulfonylamino)-hexanoic acid;

2-(Dibenzofuran-2-sulfonylamino)-6-(2-phenyl-ethenesulfonylamino)-hexanoic acid;

2-(Dibenzofuran-2-sulfonylamino)-6-isobutoxycarbonylamino-hexanoic acid;

2-(Dibenzofuran-2-sulfonylamino)-6-(9H-fluoren-9-ylmethoxycarbonylamino)-hexanoic acid;

6-(Adamantan-1-yloxycarbonylamino)-2-(dibenzofuran-2-sulfonylamino)-hexanoic acid;

6-Allyloxycarbonylamino-2-(dibenzofuran-2-sulfonylamino)hexanoic acid;

2-(Dibenzofuran-2-sulfonylamino)-4-(2-pyridin-4-yl-ethylcarbamoyl)-butyric acid;

2-(Dibenzofuran-2-sulfonylamino)-4-(2-methyl-butylcarbamoyl)-butyric acid;

2-(Dibenzofuran-2-sulfonylamino)-4-(2-hydroxy-propylcarbamoyl)-butyric acid;

2-(Dibenzofuran-2-sulfonylamino)-4-(4-propyl-phenylcarbamoyl)-butyric acid;

2-(Dibenzofuran-2-sulfonylamino)-4-(2,2-diphenyl-ethylcarbamoyl)-butyric acid;

4-Cyclopropylcarbamoyl-2-(dibenzofuran-2-sulfonylamino)-butyric acid;

2-(Dibenzofuran-2-sulfonylamino)-4-[(thiophen-2-ylmethyl)-carbamoyl]-butyric acid;

2-(Dibenzofuran-2-sulfonylamino)-4-(1,3-dimethyl-butylcarbamoyl)-butyric acid;

2-(Dibenzofuran-2-sulfonylamino)-4-(2-dimethylainino-ethylcarbamoyl)-butyric acid;

4-Benzylcarbamoyl-2-(dibenzofuran-2-sulfonylamino)-butyric acid;

2-(Dibenzofuran-2-sulfonylamino)-4-(2-thiophen-2-yl-ethylcarbamoyl)-butyric acid;

4-(4-Chloro-phenylcarbamoyl)-2-(dibenzofuran-2-sulfonylamino)-butyric acid;

2-(Dibenzofuran-2-sulfonylamino)-4-(4-phenyl-butylcarbanoyl)-butyric acid;

2-(Dibenzofuran-2-sulfonylamino)-4-[2-(1-methyl-1H-pyrrol-2-yl)-ethylcarbamoyl]-butyric acid;

2-(Dibenzofuran-2-sulfonylamino)-4-(2-methoxy-benzylcarbamoyl)-butyric acid;

2-(Dibenzofuran-2-sulfonylamino)-4-(naphthalen-1-ylmethyl)-carbamoyl]-butyric acid;

6-Benzyloxycarbonylamino-2-(dibenzofuran-2-sulfonylamino)hexanoic acid;

2-(Dibenzofuran-2-sulfonylamino)-pentanedioic acid 1-tert-butyl ester;

2-(Dibenzofuran-2-sulfonylamino)-4-phenethylcarbamoyl-butyric acid;

2-Dibenzofuran-2-sulfonylamino)-4-oxo-4-(4-propyl-phenyl)-butyric acid;

2-(Dibenzothiophene-2-sulfonylamino)-4-phenyl-butyric acid;

3-(4-tert-Butoxy-phenyl)-2-(dibenzofuran-2-sulfonylamino)-propionic acid;

3-Benzyloxy-2-(dibenzofuran-2-sulfonylamino)-propionic acid;

2-(Dibenzofuran-2-sulfonylamino)-5-(toluene-4-sulfonylamino)-pentanoic acid;

5-Benzyloxycarbonylamino-2-(dibenzofuran-2-sulfonylamino)-pentanoic acid;

2-(Dibenzofuran-2-sulfonylamino)-butyric acid;

3-tert-Butoxy-2-(dibenzofuran-2-sulfonylamino)-propionic acid;

(Dibenzofuran-2-sulfonylamino)phenyl-acetic acid; and 2-(Dibenzofuran-2-sulfonylamino)-3-(4-fluorophenyl)-propionic acid.

DETAILED DESCRIPTION OF THE INVENTION

A compound of Formula I

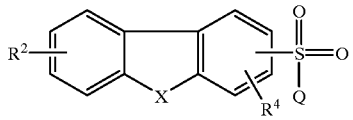

I wherein Q is an un-natural amino acid;

X is O, S, S(O)$_n$, CH$_2$, CO, or NR$^{33}$;

R$^{33}$ is hydrogen, C$_1$–C$_6$ alkyl, or C$_1$–C$_6$ alkyl-phenyl;

R$^2$ and R$^4$ are independently hydrogen, C$_1$–C$_5$ alkyl, phenyl, —NO$_2$, halogen, —OR$^5$, —CN, —CO$_2$R$^5$, —SO$_3$R$^5$, —CHO, —COR$^5$, —CONR$^5$R$^6$, —(CH$_2$)$_n$NR$^5$R$^6$, —CF$_3$, or —NHCOR$^5$;

each R$^5$ and R$^6$ are independently hydrogen or C$_1$–C$_5$ alkyl; and n is 0 to 2, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkene" means a straight or branched hydrocarbon having one or more carbon-carbon double bond.

The term "alkyne" means a straight or branched hydrocarbon having one or more carbon-carbon triple bond.

The term "cycloalkyl" means a cyclic hydrocarbon. Examples of cycloalkyl groups include cyclopropane, cyclobutane, cyclopentane, cyclohexane, and cyclooctane.

The term "aryl" means an aromatic hydrocarbon. Representative examples of aryl groups include phenyl and naphthyl.

The term "phenyl" also includes substituted phenyl wherein one or more hydrogen atom on the phenyl ring is replaced with an organic radical. Exanples of suitable substituents include, but are not limited to, halogen, C$_1$–C$_6$ alkoxy, —CF$_3$, —NO$_2$, —CN, —NH$_2$, —NH(C$_1$–C$_6$alkyl), or —N(C$_1$–C$_6$alkyl)$_2$.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl groups include, but are not limited to, 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, or 2-, 3-, 4-, 5-, 6-, or 7-indoxyl.

The aryl or heteroaryl groups may be substituted with one or more substituents, which can be the same or different. Examples of suitable substituents include alkyl, alkoxy, thioalkoxy, hydroxy, halogen, trifluoromethyl, amino, alkylamino, dialkylamino, —NO$_2$, —CN, —CO$_2$H, —CO$_2$ alkyl, —SO$_3$H, —CHO, —CO alkyl, —CONH$_2$, —CONH-alkyl, —CONHRq, —CON(alkyl)$_2$, —(CH$_2$)$_n$—NH$_2$, where n is 1 to 5 and —(CH$_2$)$_n$—NH-alkyl, —NHRq, or —NHCORq, and Rq is hydrogen or alkyl.

The symbol "—" means a bond.

An "un-natural amino acid" is an amino acid having the general structure

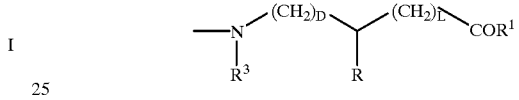

R$^3$ is hydrogen, C$_1$–C$_6$ alkyl, phenyl-C$_1$–C$_6$ alkyl wherein phenyl is unsubstituted or substituted by C$_1$–C$_6$ alkyl, alkoxy, halogen or trifluoromethyl; phenyl which is unsubstituted or mono-, di-, or tri-substituted by alkoxy, hydroxy, halogen, C$_1$–C$_6$ alkyl, cyano, nitro, trifluoromethyl, C$_1$–C$_6$ alkyl-(thio, sulfinyl or sulfonyl), amino, mono- or di-C$_1$–C$_6$ alkylamino or, on adjacent carbon atoms, by C$_1$–C$_2$-alkylenedioxy or oxy-C$_2$–C$_3$-alkylene; or a heteroaryl radical selected from pyridyl, tetrazolyl, triazolyl, thiazolyl, thienyl, imidazolyl and quinolinyl, each unsubstituted or mono- or disubstituted by C$_1$–C$_6$ alkyl or halogen; biphenyl which is unsubstituted or substituted by C$_1$–C$_6$ alkyl, alkoxy, halogen, trifluoromethyl or cyano; biphenyl-C$_1$–C$_6$ alkyl wherein biphenyl is unsubstituted or substituted by C$_1$–C$_6$ alkyl, alkoxy, halogen, trifluoromethyl or cyano; (pyridyl, thienyl, quinolinyl or thiazolyl)-C$_1$–C$_6$ alkyl, trifluoromethyl, C$_3$–C$_7$-cycloalkyl, C$_3$–C$_7$-cycloalkyl-C$_1$–C$_6$ alkyl, (oxa or thia)-C$_3$–C$_6$-cycloalkyl, [(oxa or thia)-C3–C6-cycloalkyl]-C$_1$–C$_6$ alkyl, hydroxy-C$_1$–C$_6$ alkyl, alkanoyloxy-C$_1$–C$_6$ alkyl, alkoxy-C$_1$–C$_6$ alkyl, C$_1$–C$_6$ alkyl-(thio, sulfinyl or sulfonyl)-C$_1$–C$_6$ alkyl, (amino, mono- or di-C$_1$–C$_6$ alkylamino)-C$_1$–C$_6$ alkyl, alkanoylamino-C$_1$–C$_6$ alkyl, (N-C$_1$–C$_6$ alkyl-piperazino or N-phenyl-C$_1$–C$_6$ alkylpiperazino)-C$_1$–C$_6$ alkyl or (morpholino, thiomorpholino, piperidino, pyrrolidino, piperidyl or N—C$_1$–C$_6$ alkylpiperidyl)-C$_1$–C$_6$ alkyl.

R$^1$ is C$_1$–C$_5$ alkoxy, hydroxy, or -NHOR$^5$, where R$^5$ is as defmed above. R is the side chain of an un-natural amino acid Un-natural amino acids are well-known in the art. See, for example, Roberts D. C., et al., "Unusual amino acids in peptide synthesis", The Peptides, 1993;5:341429. Un-natural amino acids are those amino acids not naturally found in living organisms. Examples of side chains of non-natural amino acids include when where R is hydrogen, —(CH$_2$)$_n$-naphthalimide, —(CH$_2$)$_n$-phthalimide, —(CH$_2$)$_n$-aryl, C$_1$–C$_6$ substituted alkyl wherein the substituent is —OH, —SH, OR', SR', halogen, —NH$_2$, —NHR, NHR', NR'R", —CO$_2$H, COR', CHO, CONH$_2$, CONHR', or CONR"R, $C_1$–$C_6$ alkyl,
aryl,
—$(CH_2)_n$-phenyl,
$C_1$–$C_6$ alkenyl,
—$(CH_2)_n$-heteroaryl,
heteroaryl, or heterocycle;

D is 0 to 3;

L is 0 to 3; and each R' and R" are independently $C_1$–$C_6$ alkyl or hydrogen and n is as defined above.

The functional groups in the amino acid side chains can be protected. For example, carboxyl groups can be esterified, amino groups can be converted to amides or carbamates, hydroxyl groups can be converted to ethers or esters, and thiol groups can be converted to thioethers or thioesters.

The compounds of Formula I or II can be administered to a patient either alone or as part of a pharmaceutically acceptable composition. The compositions can be administered to patients such as humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrrhydrofurfuryl alcohol, polyethyleneglycols and fatty acid esters of sorbitan or mixtures of these substances, and the like.

Besides such inert diluents, the composition can also include adjuvants such as wetting agents, emulsifying and suspending agents, sweetening, flavoring, and perfirming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can typically be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well-known to those skilled in the art. The term "patient" includes humans and animals.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylaamine, dimethylamine, trimethylamine, triethylamine, ethylamine and the like. See, for example, Berge S. M., et al., "Pharmaceutical Salts," *J. Pharm. Sci.*, 1977;66:1–19 which is incorporated herein by reference.

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Perganion Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention are administered to a patient in need of matrix metalloproteinase inhibition. In general, patients in need of matrix metalloproteinase inhibition are those patients having a disease or condition in which a matrix metalloproteinase plays a role. Examples of such diseases include, but are not limited to, multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

In a preferred embodiment, the matrix metalloproteinase is stromelysin-1 or gelatinase-A.

A "therapeutically effective amount" is an amount of a compound of Formula I or II that when administered to a patient having a disease that can be treated with a compound of Formula I or II ameliorates a symptom of the disease. A therapeutically effective amount of a compound of Formula I or II is readily determined by one skilled in the art by administering a compound of Formula I or II to a patient and observing the results.

The following examples illustrate particular embodiments of the invention and are not intended to limit the scope of the specification and claims in any manner.

EXAMPLES

General Synthetic Schemes

The compounds of the present invention can be synthesized using a number of different synthetic routes. Referring to General Scheme 1 the common starting materials are the sulfonyl chlorides (1). These are easily synthesized by anyone skilled in the art by sulfonation of the parent heterocycle. Some representative procedures are as follows. For dibenzofuran (1, X=O) and dibenzothiophene (1, X=S), the parent heterocycle is sulfonated at the 2-position using one equivalent of chlorosulfonic acid in chloroform at 0° C. according to the method of Bassin, et al., *Phosphorus, Sulfur and Silicon*, 1992;72:157–170). The sulfonic acid is then converted to the corresponding sulfonyl chloride (1, X=O,S) by treatment with phosphorus pentachloride at 170–180° C. For carbazole (1, X=NH), the parent heterocycle is sulfonated at the 3-position using sulfiric acid at 100° C. followed by neutralization with barium carbonate to yield the barium salt of the corresponding sulfonic acid according to the method of Loza, et al., *Sb. Mater.Nauch.—Tekh. Konf. Ukrain. Zaoch. Poitekh. Inst. Vith, Kharkov*, 1966:202–5). The sulfonic acid is then converted to the corresponding sulfonyl chloride (1, X=NH) by treatment with phosphorus pentachloride at 170–180° C. or reaction with either phosphoryl chloride, thionyl chloride, or oxalyl chloride. For fluorene (1, X=$CH_2$), according to the method of Chrzaszczewska, et al., *Lodz. Tow. Nauk., Wydz. 3, Acta Chim.*, 1966;11:143–55, the parent carbocycle is sulfonated at the 2-position using one equivalent of chlorosulfonic acid in chloroform at 0° C. followed by neutralization with potassium hydroxide to give the potassium salt of the corresponding sulfonic acid. This fluorene derivative can then be oxidized using aqueous potassium permanganate at 80° C. to the corresponding fluorenone derivative (1, X=CO). The sulfonic acid salts are then converted to the sulfonyl chloride (1, X=$CH_2$, CO) by treatment with phosphorus pentachloride and phosphoryl chloride in chloroform.

In Method A, the sulfonyl chloride (1) is condensed directly with the natural amino acid using a base such as triethylamine (TEA) in a mixture of tetrahydrofuran(THIF) and water (3:5) at 10° C. to yield the desired compound (2).

The corresponding hydroxamic acid (5) can be conveniently prepared by coupling the acid (2) with an O-protected (usually benzyl) hydroxylamine using dicyclohexylcarbodiimide (DCC) as the coupling agent in dichloromethane at temperatures ranging from −(10) to 0° C. The protecting group can be removed from compound (4) by catalytic hydrogenolysis using hydrogen gas at 50 psi and Pd/BaSO$_4$ in aqueous methanol to yield the hydroxamic acid derivative (5).

In Method B, the sulfonyl chloride (1) is condensed with a suitably C-protected (usually tertiary butyl ester) amino acid using a base such as N-methylmorpholine (NMM) in a solvent such as dichloromethane at 0° C. to yield compound (3). The protecting group can be removed from the carboxylic acid by treatment with trifluoroacetic acid in dichloromethane at 25–35° C. using anisole as a carbocation scavenger to yield (2).

Referring to General Scheme 2, compounds of the present invention (both N-substituted and N-unsubstituted sulfonamides) can also be synthesized by alkylation of the amino nitrogen of a sulfonamide of formula (6) with an amine alkylating agent of formula (7) to yield 9, wherein any substituents which are potentially reactive in the alkylation reaction may themselves be protected from such reaction. Compounds of formula 9 can then be hydrolyzed to the compounds of this present invention by basic hydrolysis using an alkali metal hydroxide such as sodium hydroxide in a solvent mixture such as THF and water. $R^1$ is typically a carboxylic acid protecting group (such as a methyl or ethyl ester). Leaving groups (Z) are well known in the art and include halogen atoms (such as bromine) and triflate. Sulfonamides of formula (6) may be prepared by standard methods, including the reaction of an amine of formula (8) with the sulfonyl chloride (1).

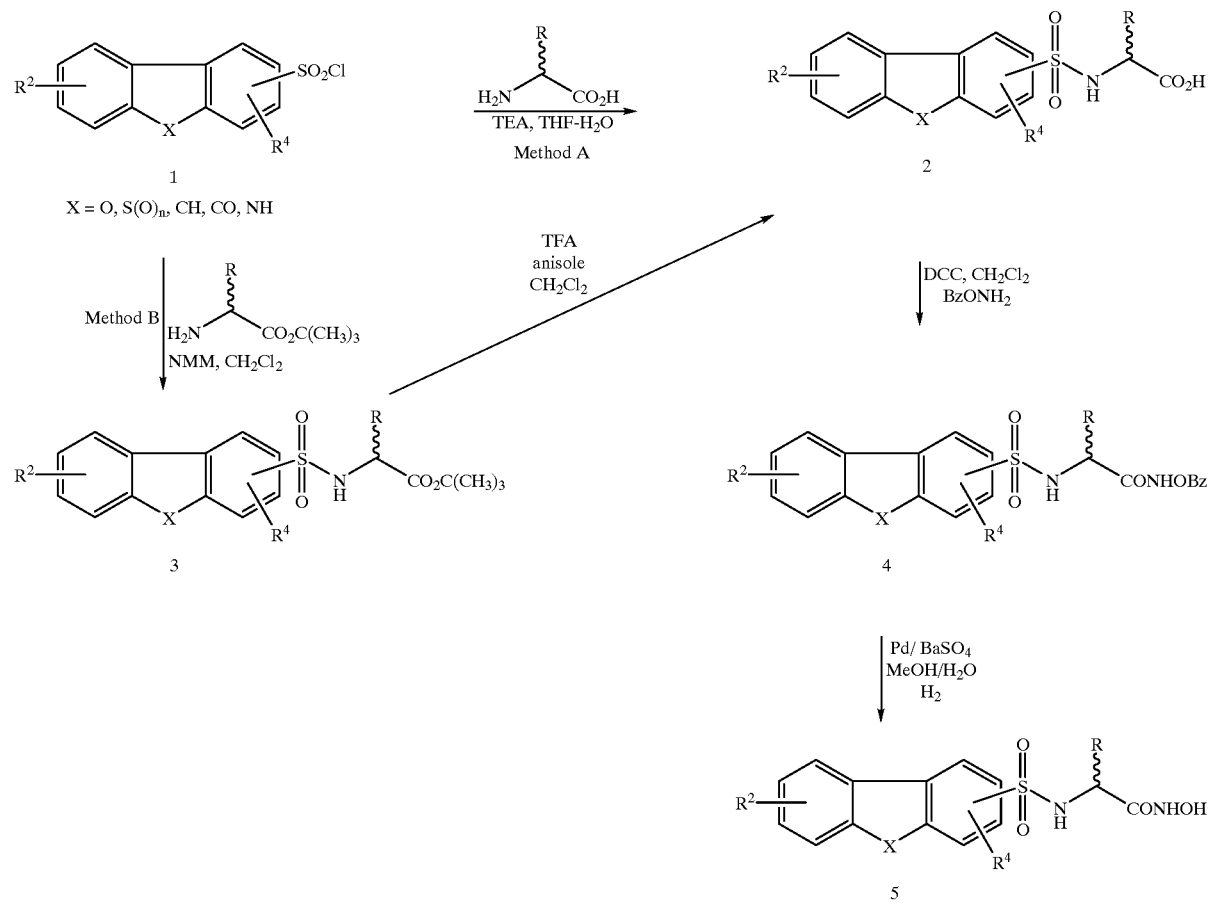

General Scheme 1

TEA = triethylamine
THF = tetrahydrofuran
NMM = N-methylmorpholine
DCC = dicyclohexylcarbodiimide
Bz = benzyl
MeOH = methanol

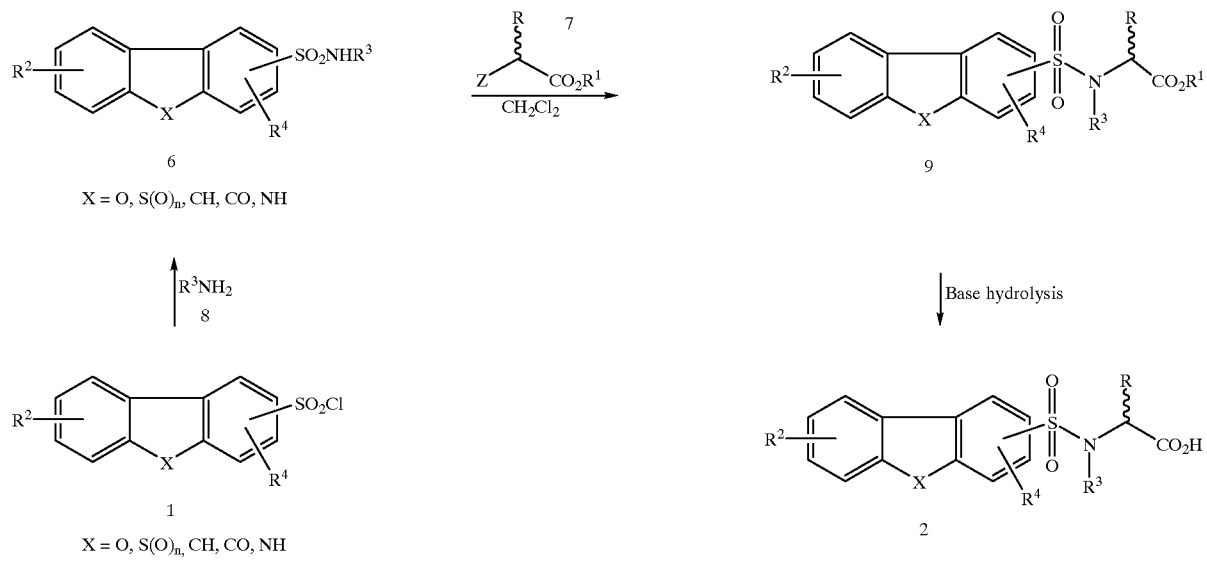

General Scheme 2

Example 1

(S)-2-(Dibenzofuran-2-sulfonylamino)-4-phenyl-butyric acid

To a THF/water (5:3, 8 mL) solution of (S)α-amino4-phenyl-butyric acid (0.61 g, 0.0034 mol) and triethylamine (1 mL) at 10° C. was added dibenzofuran-2-sulfonyl chloride (1.0 g, 0.00375 mol) in one portion with stirring. The resulting solution was stirred at room temperature for 24 hours. The solution was then concentrated in vacuo and the residue redissolved in water (10 mL). This solution was cooled in an ice bath and then acidified with 1N HCl. An oil was deposited, which was then triturated with ethyl acetate and hexane to give the title product (0.54 g, 35%), Melting point=130–132° C.

Following the general procedure of Example 1, the following compound was obtained.

Example 2

2(S)-3-[(Dibenzofuran-2-sulfonylamino)-methyl]-5-methyl-hexanoic acid,

Melting point=125–128° C.
Parallel Array Synthesis of Examples A1—A40

The appropriate carboxylic acid (1.5 equivalents, 0.18 mmol), 70 mg of a morpholino-resin (prepared according to Booth R. J. and Hodges J. C., *J. Am. Chem. Soc.*, 1997;119 (21):4882–4886) and 1 mL of a 0.18 M solution of isobutylchloroformate in dichloromethane was added to each of 40 different vials. This was shaken for 1 hour and then 1 mL of a 0.12 M stock solution of 6-amino-2-(dibenzofuran-2-sulfonylamino)-hexanoic acid methyl ester hydrobromide in triethylamine was added to each of the vials. The vials were sealed and shaken for 16 hous at room temperature. An excess of an amino-resin and an isocyanato-resin (also both prepared according to Booth and Hodges, Supra., 1997) was added to each vial and shaken for 16 hours to quench unreacted starting materials. Each reaction was filtered through a plug of glass wool, and the resins were washed with 2 mL tetrahydrofuran. The filtrate was evaporated under a stream of nitrogen, and the residue in each vial was redissolved in 1 mL dioxane. One milliliter of a 0.6 M aqueous solution of lithium hydroxide was added, and the resulting mixtures were shaken for 16 hours. Each reaction was washed with diethyl ether and the aqueous layer was then acidified with 1 molar hydrochloric acid. The reactions were extracted with ethyl acetate and evaporated under a stream of nitrogen to leave the expected products. The compounds were analyzed by liquid chromatography/mass spectrometry (LC/MS) to determine purity and presence of expected molecular ion.

Example A1
6-[2-(4-Chloro-phenoxy)-2-methyl-propionylamino]-2-(dibenzofuran-2-sulfonylamino)-hexanoic acid

Example A2
2-(Dibenzofuran-2-sulfonylamino)-6-[2-(pyridin4-lysulfanyl)-acetylamino]-hexanoic acid

Example A3
2-(Dibenzofuran-2-sulfonylamino)-6-[2-(2,4-dichloro-phenoxy)-acetylamino]-hexanoic acid

Example A4
2-(Dibenzofuran-2-sulfonylamino)-6-[2-(2-trifluoromethyl-phenyl)-acetylamino]-hexanoic acid

Example A5
2-(Dibenzofuran-2-sulfonylamino)-6-(2-thiophen-2-yl-acetylamino)-hexanoic acid

Example A6
2-(Dibenzofuran-2-sulfonylamino)-6-(2-phenoxy-butrylamino)-hexanoic acid

Example A7
2-(Dibenzofuran-2-sulfonylamino)-6-(phenylsulfanyl-acetylamino)-hexanoic acid

Example A8
2-(Dibenzofuran-2-sulfonylamino)-6-(2-phenoxy-acetylamino)-hexanoic acid

Example A9
2-(Dibenzofuran-2-sulfonylamino)-6-[2-(3,4-dimethoxy-phenyl)-acetylamino]-hexanoic acid

Example A10
6-[2-(4-tert-Butyl-phenoxy)actylamino]-2-(dibenzofuran-2-sulfonylamino)-hexanoic acid

Example A11
2-(Dibenzofuran-2-sulfonylamino)-6-[3-(3,4-dimethoxy-phenyl)-propionylamino]-hexanoic acid

Example A12
6-(2-(Cyclopent-1-enyl-acetylamino)-2-(dibenzofuran-2-sulfonylamino)-hexanoic acid

Example A13
2-(Dibenzofuran-2-sulfonylamino)-6-[2-(4-methoxy-phenoxy)-acetylamino]-hexanoic acid

Example A14
2-(Dibenzofuran-2-sulfonylamino)-6-[2-(naphthalen-1-yloxy)acetylamino]-hexanoic acid

Example A15
2-(Dibenzofuran-2-sulfonylamino)-6-[2-(4nitro-phenoxy)-acetylamino]-hexanoic acid

Example A16
6-[4-(4-Chloro-3-methyl-phenoxy)-butyrylamino]-2-(dibenzofuran-2-sulfonylamino)-hexanoic acid

Example A17
2-(Dibenzofuran-2-sulfonylamino)-6-[3-(4-methoxy-phenyl)-propionylamino]-hexanoic acid

Example A18
2-(Dibenzofuran-2-sulfonylamino)-6-(2-pyridin-3-yl-acetylamino)-hexanoic acid

Example A19
6-(2-Benzo[1,3]dioxol-5-yl-acetylamino)-2-(dibenzofuran-2-sulfonylamino)-hexanoic acid

Example A20
2-(Dibenzofuran-2-sulfonylamino)-6-(2-pyridin-2-yl-acetylamino)-hexanoic acid

Example A21
2-(Dibenzofuran-2-sulfonylamino)-6-[4-(4-nitro-phenyl)-butyrylamino]-hexanoic acid

Example A22
2-(Dibenzofuran-2-sulfonylamino)-6-(3-pyridin4-yl-propionylamino)-hexanoic Acid

Example A23
2-(Dibenzofuran-2-sulfonylamino)-(2-phenylamino-acetylamino)-hexanoic acid

Example A24
2-(Dibenzofuran-2-sulfonylamino)-6-(2-indol-1-yl-acetylamino)-hexanoic acid

Example A25
2-(Dibenzofuran-2-sulfonylamino-6-[3-(2-methoxy-phenyl)-propionylamino]-hexanoic acid

Example A26
2-(Dibenzofuran-2-sulfonylamino)-6-(4-phenyl-butyrylamino)-hexanoic acid

Example A27
2-(Dibenzofuran-2-sulfonylamino)-6-(3-p-tolyl-propionylamino)-hexanoic acid

Example A28
6-[3-(4-Chloro-phenyl)-propionylamino]-2-(dibenzofuran-2-sulfonylamino)-hexanoic acid

Example A29
6-[2-(2-Benzyloxy-phenyl)acetylamino]-2-(dibenzofuran-2-sulfonylamino)-hexanoic acid

Example A30
2-(Dibenzofuran-2-sulfonylamino)-6-[2-naphthalen-2-yl-acetylamino)-hexanoic acid

Example A31
2-(Dibenzofuran-2-sulfonylamino)-6-(4-1H-indol-3-yl-butyrylamino)-hexanoic acid

Example A32
2-(Dibenzofuran-2-sulfonylamino)-6-(2-naphthalen-1-yl-acetylamino)-hexanoic acid

Example A33
6-[3-(4-Chloro-phenoxy)-propionylamino]-2-(cibenzofuran-2-sulfonylamino)-hexanoic acid

Example A34
2-(Dibenzofuran-2-sulfonylamino)-6-(6-phenyl-hexanoylamino)-hexanoic acid Example A35
2-(Dibenzofuran-2-sulfonylamino)-6-[4-thiophen-2-yl-butyrylamino)-hexanoic acid Example A36
2-(Dibenzofuran-2-sulfonylamino)-6-(3,3,3-triphenyl-propionylamino)-hexanoic acid Example A37
2-(Dibenzofuran-2-sulfonylamino)-6-(3-diethylamino-propionylamino)-hexanoic acid Example A38
2-(Dibenzofuran-2-sulfonylamino)-6-(1-phenyl-cyclopropane carbonylamino)-hexanoic acid Example A39
6-(3-Benzo[1,3dioxol-5-yl-propionylamino)-2-(dibenzofuran-2-sulfonylamino)-hexanoic acid Example A40
6-[(Cyclopentyl-phenyl-acetyl)-amino]-2-(dibenzofuran-2-sulfonylamino)hexanoic acid Parallel Array Synthesis of Examples B1–B10

The appropriate isocyanate or isothiocyanate (1.5 equivalents, 0.18 mmol) 70 mg of a morpholino-resin (prepared according to Booth and Hodges, Supra., 1997) were mixed in 1 mL dichloromethane in each of 10 different vials. One milliliter of a 0.12 M stock solution of 6-amino-2-(dibenzofuran-2-sulfonylamino)-hexanoic acid methyl ester hydrobromide in triethylamine was added to each of the vials. The vials were sealed and shaken for 16 hours at room temperature. An excess of an amino-resin and an isocyanato-resin (also both prepared according to Booth and Hodges, Supra., 1997) was added to each vial and shaken for 16 hours to quench unreacted starting materials. Each reaction was filtered through a plug of glass wool, and the resins were washed with 2 mL tetrahydrofuran. The filtrate was evaporated under a stream of nitrogen, and the residue in each vial was redissolved in 1 mL dioxane. One milliliter of a 0.6 M aqueous solution of lithium hydroxide was added, and the resulting mixtures were shaken for 16 hours. Each reaction was washed with diethyl ether, and the aqueous layer was then acidified with 1 molar hydrochloric acid. The reactions were extracted with ethyl acetate and evaporated under a stream of nitrogen to leave the expected products. The compounds were analyzed by LCIMS to determine purity and presence of expected molecular ion.

Example B1
2-(Dibenzofuran-2-sulfonylamino)-6-[3-(4-methoxy-phenyl)-ureido]-hexanoic acid Example B2
2-(Dibenzofuran-2-sulfonylamino)-6-[3-(3,4dichloro-phenyl)-ureido]-hexanoic acid Example B3
2-(Dibenzofuran-2-sulfonylamino)-6-(3-pyridin-3-yl-thioureido)-hexanoic acid Example B4 6-(3-Benzhydryl-thioureido)-2-(dibenzofiuran-2-sulfonylamino)-hexanoic acid Example B5
6-(3-Benzyl-thioureido)-2-(dibenzofuran-2-sulfonylamino)-hexanoic acid Example B6
6-(3-Adamantan-1-yl-thioureido)-2-(dibenzofuran-2-sulfonylamino)-hexanoic acid Example B7
2-(Dibenzofuran-2-sulfonylamino)-6-(3-naphthalen-2-yl-thioureido)-hexanoic acid Example B8
6-(3-Allyl-ureido)-2-(dibenzofuran-2-sulfonylamino)-hexanoic acid Example B9
6-(3-Benzyl-ureido)-2-(dibenzofuran-2-sulfonylamino)-hexanoic acid Example B10
2-(Dibenzofuran-2-sulfonylamino)-6-(3-phenyl-ureido)-hexanoic acid Parallel Array Synthesis of Examples C1–C6

The appropriate acyl chloride (1.5 equivalents, 0.18 mmol) and 70 mg of a morpholino-resin (prepared according to Booth and Hodges, Supra., 1997) were mixed in 1 mL dichloromethane in each of 6 different vials. One milliliter of a 0.12 M stock solution of 6-amino-2-(dibenzofuran-2-sulfonylamino)-hexanoic acid methyl ester hydrobromide in triethylamine was added to each of the vials. The vials were sealed and shaken for 16 hours at room temperature. An excess of an amino-resin and an isocyanato-resin (also both prepared according to Booth and Hodges, Supra., 1997) was added to each vial and shaken for 16 hours to quench unreacted starting materials. Each reaction was filtered through a plug of glass wool, and the resins were washed with 2 mL tetrahydrofuran. The filtrate was evaporated under a stream of nitrogen, and the residue in each vial was redissolved in 1 mL dioxane. One milliliter of a 0.6 M aqueous solution of lithium hydroxide was added, and the resulting mixtures were shaken for 16 hours. Each reaction was washed with diethyl ether, and the aqueous layer was then acidified with 1 molar hydrochloric acid. The reactions were extracted with ethyl acetate and evaporated under a stream of nitrogen to leave the expected products. The compounds were analyzed by LC/MS to determine purity and presence of expected molecular ion.

Example C1
2-(Dibenzofuran-2-sulfonylamino)-6-(3-phenyl-acryloylamino)-hexanoic acid Example C2
2-(Dibenzofuran-2-sulfonylamino)-6-phenylacetylamino-hexanoic acid Example C3
2-(Dibenzofuran-2-sulfonylamino)-6-(3-phenyl-propionylamino)-hexanoic acid Example C4
6-[2-(4-Chloro-phenoxy)-acetylamino]-2-(dibenzofuran-2-sulfonylamino)-hexanoic acid Example C5
2-(Dibenzofuran-2-sulfonylamino)-6-[2-(2,4,6-triisopropyl-phenyl)-acetylamino]-hexanoic acid Example C6
2-(Dibenzofuran-2-sulfonylamino)-6-(2-phenyl-butyrylamino)-hexanoic acid Parallel Array Synthesis of Examples D1–D10

The appropriate sulfonyl chloride (1.5 equivalents, 0.18 mmol) and 70 mg of a morpholino-resin (prepared according to Booth and Hodges, Supra., 1997) were mixed in 1 mL dichloromethane in each of 10 different vials. One milliliter of a 0.12 M stock solution of 6-amino-2-(dibenzofuran-2-sulfonylamino)-hexanoic acid methyl ester hydrobromide in triethylamine was added to each of the vials. The vials were sealed and shaken for 16 hours at room temperature. An excess of an amino-resin and an isocyanato-resin (also both prepared according to Booth and Hodges, Supra, 1997) was added to each vial and shaken for 16 hours to quench unreacted starting materials. Each reaction was filtered through a plug of glass wool, and the resins were washed with 2 mL tetrahydrofuran. The filtrate was evaporated under a stream of nitrogen, and the residue in each vial was redissolved in 1 mL dioxane. One milliliter of a 0.6 M aqueous solution of lithium hydroxide was added, and the resulting mixtures were shaken for 16 hours. Each reaction was washed with diethyl ether, and the aqueous layer was then acidified with 1 molar hydrochloric acid. The reactions were extracted with ethyl acetate and evaporated under a stream of nitrogen to leave the expected products. The compounds were analyzed by LC/MS to determine purity and presence of expected molecular ion.

Example D1

2-(Dibenzofuran-2-sulfonylamino)-6-(4-fluoro-benzenesulfonylamino)-hexanoic acid Example D2

2-(Dibenzofuran-2-sulfonylamino)-6-(4-methoxy-benzenesulfonylamino)-hexanoic acid Example D3

6-(4-Bromo-benzenesulfonylamino)-2-(dibenzofuran-2-sulfonylamino)-hexanoic acid

Example D4

6-(2-Acetylamino-thiazole-5-sulfonylamino)-2-(dibenzofuran-2-sulfonylamino)-hexanoic acid Example D5

6-(4-Acetylamino-benzensulfonylamino)-2-(dibenzofuran-2-sulfonylamino)-hexanoic acid Example D6

6-Benzenesulfonylamino-2-(dibenzofuran-2-sulfonylamino)-hexanoic acid

Example D7

6-(Butane-1-sulfonylamino)-2-(dibenzofuran-2-sulfonylamino)-hexanoic acid

Example D8

2-(Dibenzofuran-2-sulfonylamino)-6-(naphthalene-2-sulfonylamino)-hexanoic acid

Example D9

2-(Dibenzofuran-2-sulfonylamino)-6-(naphthalene-1-sulfonylamino)-hexanoic acid

Example D10

2-(Dibenzofuran-2-sulfonylamino)-6-(2-phenyl-ethenesulfonylamino)-hexanoic acid

Parallel Array Synthesis of Examples E1–E4

The appropriate carbamoyl halide (1.5 equivalents, 0.18 mmol) and 70 mg of a morpholino-resin (prepared according to Booth and Hodges, Supra., 1997) =15 were mixed in 1 mL dichloromethane in each of 4 different vials. One milliliter of a 0.12 M stock solution of 6-amino-2-(dibenzofuran-2-sulfonylamino)-hexanoic acid methyl ester hydrobromide in triethylamine was added to each of the vials. The vials were sealed and shaken for 16 hours at room temperature. An excess of an amino-resin and an isocyanato-resin (also both prepared according to Booth and Hodges, Supra., 1997) was added to each vial and shaken for 16 hours to quench unreacted starting materials. Each reaction was filtered through a plug of glass wool, and the resins were washed with 2 mL tetrahydrofuran. The filtrate was evaporated under a stream of nitrogen, and the residue in each vial was redissolved in 1 mL dioxane. One milliliter of a 0.6 M aqueous solution of lithium hydroxide was added, and the resulting mixtures were shaken for 16 hours. Each reaction was washed with diethyl ether, and the aqueous layer was then acidified with 1 molar hydrochloric acid. The reactions were extracted with ethyl acetate and evaporated under a stream of nitrogen to leave the expected products. The compounds were analyzed by LC/MS to determine purity and presence of expected molecular ion.

Example E1

2-(Dibenzofuran-2-sulfonylamino)-6-isobutoxycarbonylamino-hexanoic acid

Example E2

2-(Dibenzofuran-2-sulfonylamino)-6-(9H-fluoren-9-ylmethoxycarbonylamino)-hexanoic acid Example E3

6-(Adamantan-1-yloxycarbonylamino)-2-(dibenzofuran-2-sulfonylamino)-hexanoic acid Example E4

6-Allyloxycarbonylamino-2-(dibenzofuran-2-sulfonylamino)-hexanoic acid

Parallel Array synthesis of Examples F1–F16

The appropriate amine (1.0 equivalent, 0.096 mmol) and 70 mg of a morpholino-resin (prepared according to Booth and Hodges, Supra., 1997) were mixed in 1 mL dichloromethane in each of 16 different vials. One milliliter of a 0.096 M stock solution (S)-2-(dibenzofiuran-2-sulfonylamino)-pentanedioic acid, 5-acyl chloride, and 1-methyl ester in dichloromethane was added to each of the vials. The vials were sealed and shaken for 14 days at room temperature. An excess of an amino-resin and an isocyanato-resin (also both prepared according to Booth and Hodges, Supra., 1997) was added to each vial and shaken for 16 hours to quench unreacted starting materials. Each reaction was filtered through a plug of glass wool, and the resins were washed with 2 mL tetrahydrofuran. The filtrate was evaporated under a stream of nitrogen, and the residue in each vial was re-dissolved in 1 mL dioxane. One milliliter of a 0.6 M aqueous solution of lithium hydroxide was added, and the resulting mixtures were shaken for 16 hours. Each reaction was washed with diethyl ether, and the aqueous layer was then acidified with 1 molar hydrochloric acid. The reactions were extracted with ethyl acetate and evaporated under a stream of nitrogen to leave the expected products. The compounds were analyzed by LC/MS to determine purity and presence of expected molecular ion.

Example F1

2-(Dibenzofuran-2-sulfonylamino)-4-(2-pyridin-4-yl-ethylcarbamoyl)-butyric acid

Example F2

2-(Dibenzofuran-2-sulfonylamino)-4-(2-methyl-butylcarbamoyl)-butyric acid

Example F3

2-(Dibenzofuran-2-sulfonylamino)-4-(2-hydroxy-propylcarbamoyl)-butyric acid

Example F4

2-(Dibenzofuran-2-sulfonylamino)-4-(4-propyl-phenylcarbamoyl)-butyric acid

Example F5

2-(Dibenzofuran-2-sulfonylamino)-4-(2,2-diphenyl-ethylcarbamoyl)-butyric acid

Example F6

4-Cyclopropylcarbamoyl-2-(dibenzofuran-2-sulfonylamino)-butyric acid

Example F7

2-(Dibenzofuran-2-sulfonylamino)-4-[(thiophen-2-ylmethyl)-carbamoyl]-butyric acid

Example F8

2-(Dibenzofuran-2-sulfonylamino)-4-(1,3-dimethyl-butylcarbamoyl)-butyric acid

Example F9

2-(Dibenzofuran-2-sulfonylamino)-4-(2-dimethylamino-ethylcarbamoyl)-butyric acid

Example F10

4-Benzylcarbamoyl-2-(dibenzofuran-2-sulfonylamino)-butyric acid

Example F11

2-(Dibenzofuran-2-sulfonylamino)-4-(2-thiophen-2-yl-ethylcarbamoyl)-butyric acid

Example F12

4-(4-Chloro-phenylcarbamoyl)-2-(dibenzofuran-2-sulfonylamino)-butyric acid

Example F13

2-(Dibenzofuran-2-sulfonylamino)-4-(4-phenyl-butylcarbamoyl)-butyric acid

Example F14

2-(Dibenzofuran-2-sulfonylamino)-4-[2-(1-methyl-1H-pyrrol-2-yl)-ethylcarbamoyl]-butyric acid

Example F15

2-(Dibenzofuran-2-sulfonylamino)-4-(2-methoxy-benzylcarbamoyl)-butyric acid

Example F16

2-(Dibenzofuran-2-sulfonylamino)-4-(naphthalen-1-ylmethyl)-carbamoyl]-butyric acid Synthesis of Examples 3–9

Example 3

6-Benzyloxycarbonylamino-2-(dibenzofuran-2-sulfonylamino)-hexanoic acid

When in the procedure of Example 1, (S)α-amino-4-phenyl-butyric acid is replaced with (S)-2-amino-6-benzyloxycarbonylamino-hexanoic acid, methyl ester, and the resulting intermediate is hydrolyzed with aqueous lithium hydroxide and acidified with concentrated hydrochloric acid, the title compound is obtained; mp 133–135° C.

Example 4

2-(Dibenzofuran-2-sulfonylamino)-pentanedioic acid 1-tert-butyl Ester

When in the procedure of Example 1, (S)-α-amino-4-phenyl-butyric acid is replaced with (S)-2-amino-pentanedioic acid, 5-tert-butyl ester, 1-methyl ester, and the resulting intermediate is hydrolyzed with aqueous lithium hydroxide and acidified with concentrated hydrochloric acid, the title compound is obtained, $^1$H NMR (CDCl$_3$): δ8.45 (s, 1H), 7.98 (d, 1H), 7.90 (d, 1H), 7.63–7.60 (m, 2H), 7.54 (t, 1H), 7.41 (t, 1H), 5.49 (d, 1H1), 4.00 (m, 1H), 2.45–2.28 (m, 2H), 2.09–2.01 (m, 1H), 1.897–1.80 (m, 1H), 1.41 (s, 9H1 ppm.

Example 5

2-(Dibenzofuran-2-sulfonylamino)-4-phenethylcarbamoyl-butyric acid

When in the procedure of Example 1, (S)-α-amino-4-phenyl-butyric acid is replaced with (S)-2-amino-pentanedioic acid, 5-tert-butyl ester, 1-methyl ester, and the resulting intermediate is hydrolyzed with trifluoroacetic acid, treated with oxalyl chloride, reacted with phenethyl amine and then hydrolyzed with aqueous lithium hydroxide and acidified with concentrated hydrochloric acid, the title compound is obtained ; mp 197–201° C.

Example 6

2-Dibenzofuran-2-sulfonylamino)-4-oxo-4-(4propyl-phenyl)-butyric acid

When in the procedure of Example 1, (S)-α-amino-4-phenyl-butyric acid is replaced with (S)-2-(dibenzofran-2-sulfonylamino)-4-oxo-4-(4-propyl-phenyl)-butyric acid (*Biorg. Med. Chem. Lett.*, 1995;5:2441–2444), the title compound is obtained.

$^1$H NMR (CDCl$_3$): δ8.44 (s, 1H), 7.90 (d, 2H), 7.67 (d, 2H), 7.56–7.48 (m, 3H 7.36 (t, 1H), 7.11 (d, 2H), 6.06 (bs, 1H), 4.32 (bs, 1H), 3.643.51 (m, 2H), 2.56 (t, 2H), 1.65–1.56 (m, 2H), 0.92 (t, 3H), ppm.

Example 7

2-(Dibenzothiophene-2-sulfonylamino)-4phenyl-butyric acid

When in the procedure of Example 1 dibenzofuran-2-sulfonylchloride is replaced with dibenzothiophene-2-sulfonylchloride, the title compound is obtained; mp 148–151° C.

Example 8

(S)-2-(Dibenzothiophene-3-sulfonylamino)-4-phenyl-butyric acid

Step (a) Dibenzofuran-3-sulfonyl Chloride

3-Aminodibenzofuran (10 g, 54.6 mmol) was diazotized by dissolving in 180 mL glacial acetic acid, 50 mL water, and 14 mL concentrated hydrochloric acid at 0° C. and adding 15 mL of a 5.5 M aqueous solution of sodium nitrite. The resulting mixture was stirred for 1 hour before pouring into a solution of copper(II)chloride (2.0 g, 14.9 mmol) in 240 mL of a 1:1 mixture of benzene and glacial acetic acid saturated with sulfur dioxide. This mixture was allowed to warm to room temperature and stirred for 16 hours. The reaction was partitioned between water and chloroform. The chloroform layer was washed with water, dried over magnesium sulfate, filtered, and concentrated to give the title compound as a yellowish solid.

Step (b) (S)-2-(Dibenzothiophene-3-sulfonylamino)-4-phenyl-butyric acid

When in the procedure of Example 1 dibenzofuran-2-sulfonylchloride is replaced with dibenzofuran-3-sulfonylchloride, the title compound is obtained; mp 210–212° C.

Example 9

(S)-2-(9H-Fluorene-2-sulfonylamino)-4-phenyl-butyric acid

When in the procedure of Example 1 dibenzofuran-2-sulfonyl chloride is replaced with 9H-fluorene-2-sulfonylchloride, the title compound is obtained; mp 128–131° C.

Parallel Array Synthesis of Examples H1–H8

The appropriate un-natural amino acid ester (0.1 mmol) and 70 mg of a morpholino-resin (prepared according to Booth and Hodges, Supra., 1997) were mixed in 1 mnL dichloromethane in each of 8 different vials. Two milliliters of a 0.06 M stock solution of dibenzofuran-2-sulfonylchloride was added to each of the vials. The vials were sealed and shaken for 16 hours at room temperature. An excess of an amino-resin and an isocyanato-resin (also both prepared according to Booth and Hodges, Supra., 1997) was added to each vial and shaken for 16 hours to quench unreacted starting materials. Each reaction was filtered through a plug of glass wool, and the resins were washed with 2 mL tetrahydrofuran. The filtrate was evaporated under a stream of nitrogen, and the residue in each vial was re-dissolved in 1 mL dioxane.

Those compounds that were methyl esters were hydrolyzed by adding 1 mL of a 0.6 M aqueous solution of lithium hydroxide shaking for 16 hours. Each reaction was washed with diethyl ether, and the aqueous layer was then acidified with 1 molar hydrochloric acid. The reactions were extracted with ethyl acetate and evaporated under a stream of nitrogen to leave the expected products.

Those compounds that were t-butyl esters were hydrolyzed by adding trifluoroacetic acid and shaking for 16 hours. The trifluoroacetic acid was removed by evaporation to leave the expected products. All of the compounds were analyzed by high pressure liquid chromatography (HPLC) to determine purity.

Example H1

3-(4-tert-Butoxy-phenyl)-2-(dibenzofuran-2-sulfonylamino)-propionic acid

Example H2

3-Benzyloxy-2-(dibenzofuran-2-sulfonylamino)-propionic acid

Example H3

2-Dibenzofuran-2-sulfonylamino)-5-(toluene-4-sulfonylamino)-pentanoic acid

Example H4

5-Benzyloxycarbonylamino-2-(dibenzofuran-2-sulfonylamino)-pentanoic acid

Example H5

2-(Dibenzofuran-2-sulfonylamino)-butyric acid

Example H6

3-tert-Butoxy-2-(dibenzofuran-2-sulfonylamino)-propionic acid

Example H7

(Dibenzofuran-2-sulfonylamino)-phenyl-acetic acid

Example H8

2-(Dibenzofuran-2-sulfonylamino)-3-(4-fluorophenyl)-propionic acid

INHIBITION STUDIES

Experiments were carried out which demonstrate the efficacy of compounds of Formula I and II as potent inhibitors of stromelysin-1 and gelatinase A. Experiments were carried out with the catalytic domains, i.e., Table 1 shows the activity of the Examples with respect to both stromelysin-1 and gelatinase A, GCD (recombinant gelatinase A catalytic domain); SCD (stromelysin-1 catalytic domain). IC$_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*," *Biochemistry*, 1992;31:11231–11235). MMP01, MMP07, MMP09, and MMP13 activity was assayed in a method similar to MMP02 and MMP03 (SCD and GCD). MMP01 and MMP09 can be obtained from Washington University School of Medicine, St. Louis, Mo. MMP07 can be obtained in accordance with the known procedure set forth by Ye QZ, Johnson L. L., and Baragi V., "Gene Syntheses and Expression in *E. coli* for PUMP, a Human Matrix Metalloproteinase" *Biochem. and Biophys. Res. Comm.*, 1992; 186:143–149. MMP 13 can be obtained in accordance with the known procedure set forth by Freije J. M. P., et al., "Molecular Cloning and Expression of Collegenase-3, a Novel Human Matrix Metalloproteinase Produced by Breast Carcinomas" *J. Bio. Chem.*, 1994;269:16766–6773.

Thiopeptolide Assay

Hydrolysis of the thiopeptolide substrate Ac-Pro-Leu-Gly-thioester-Leu-Leu-Gly-OEt (Bachem) is used as the primary screen to determine $IC_{50}$ values for MMP inhibitors. A 100 μL reaction contains 1 mM 5,5'-dithiobis(2-nitrobenzoic acid) (DTNB), 100 μM substrate, 0.1% Brij, enzyme, and inhibitor in the appropriate reaction buffer. Activated full-length enzymes are assayed at 5 nM, Stromelysin Catalytic Domain (SCD) at 10 nM, and Gelatinase A Catalytic Domain (GaCD) at 1 nM. Inhibitors are screened from 100 μM to 1 nM. Full-length enzymes are assayed in 50 mM HEPES, 10 mM $CaCl_2$, pH 7.0; SCD in 50 mM MES, 10 mM $CaCl_2$, pH 6.0; and GaCD in 50 mM MOPS, 10 mM $CaCl_2$, 10 μM $ZnCl_2$, pH 7.0. The change in absorbance at 405 riM is monitored on a ThermoMax microplate reader at room temperature continuously for 20 minutes.

Ac is acetyl;

Pro is proline;

Leu is leucine;

Gly is glycine;

Et is ethyl;

HEPES is 4-(2-hydroxymethyl)piperazine-1-ethane sulfonic acid;

MES is 2-morpholinoethane sulfonic acid monohydrate; and

MOPS is 3-morpholtriopropane sulfonic acid.

Soluble Proteoglycan Assay (stromelysin natural substrate assay) SCD(PG)

Solubilized proteoglycan substrate is prepared from bovine cartilage powder (Sigma) using the method described by Nagase and Woessner in *Anal. Biochem.*, 1980;107:385–392. A 100 μL reaction contains 10 μg/mL proteoglycan, enzyme, and inhibitor in 50 mM MES, 10 mM $CaCl_2$, pH 6.0. Activated full-length stromelysin or stromelysin catalytic domain (SCD) is assayed at 100 nM. Inhibitors are screened from 100 μM to 1 nM. The reaction is incubated at 37° C. for 3 hours then stopped with the addition of 1,1 0-phenanthroline at a final concentration of 1 mM. Reaction products are separated from undigested substrate using ultrafree-MC polysulfone microcons with a 300,000 molecular weight cut-off membrane (Millipore) and quantified using a modified 1,9-dimethylene blue (DMB) assay described by Farrdale, Sayers, and Barrett in *Connective Tissue Research*, 1982;9:247–248. Absorbance is measured at 518 nm using 32 μg/mL DMB in a 1 mL reaction. The standard curve is constructed from 0 to 100 μg shark cartilage chondroitin sulfate C (Sigma).

Gelatin Assay (glatinase natural substrate assay) GDS(Gel)

Rat tail Type I collagen (Sigma) is denatured by heating at 95° C. for 20 minutes to prepare the gelatin substrate. A 50 μL reaction contains 1.12 mg/mL substrate, enzyme, inhibitor, and 80 μg/mL soy bean trypsin inhibitor as an inert internal standard in 50 mM MOPS, 10 mM $CaCl_2$, 10 μM $ZnCl_2$, pH 7.0. Activated full length gelatinase A is assayed at 1 nM and gelatinase A catalytic domain (GaCD) at 10 nM. Inhibitors are screened from 100 μM to 1 nM. The reactions are incubated at 37° C. for 30 minutes then stopped with 50 μL at 2×Tricine gel loading buffer (Novex). Reaction products are separated from undigested substrate by electrophoresis on Tricine-SDS 10–20% polyacrylamide gradient gels (Novex). Protein bands are stained with Coomassie Brilliant Blue R and quantified using a Bio Image densitometer (Millipore). $IC_{50}$ values are calculated from the disappearance of substrate using the sum of the top three bands of each reaction after normalization with the internal standard.

TABLE 1

| Example | $IC_{50}$ (μM) | | | | | |
|---|---|---|---|---|---|---|
| | MMP01 | MMP02 | MMP03 | MMP07 | MMP09 | MMP13 |
| 1 | 47 | 0.27 | 0.46 | — | 67 | — |
| 2 | — | 100 | 86 | — | — | — |
| 3 | 62 | 0.35 | 0.18 | 3.3 | — | — |
| 4 | 91 | 0.12 | 0.46 | 3.7 | — | 0.35 |
| 5 | 39 | 0.076 | 0.325 | 6.55 | — | 0.28 |
| 6 | 100 | 2.4 | 3.7 | 87 | — | 7.1 |
| 7 | 100 | 0.78 | 1.3 | 82 | — | 5.8 |
| 8 | 3.5 | 0.0038 | 0.013 | 1.2 | — | 0.032 |
| 9 | 49.5 | 0.024 | 0.0465 | 2.55 | 100 | 0.33 |

MMP Inhibitor Bioassay

Animals are dosed by gavage with either vehicle or compound at 2, 10, or 50 mg/kg. Blood samples are collected from 3–4 animals from each dosing group at 1, 2, 4, 6, and 24 hour postdose, centrifuged, and the plasma immediately frozen at -20° C. Plasma protein is precipitated with an equal volume of acetonitrile and separated by centrifugation at room temperature. The supernate is evaporated to dryness and reconstituted to the original plasma volume with 50 mM Tris, pH 7.6. Ten-fold serial dilutions of the reconstituted plasma samples are prepared in 50 mM Tris, pH 7.6 for dose response assays using the appropriate thiopeptolide assay. The concentration of plasma which yields 50% inhibition of enzyme is determined and used to calculate the inhibitor plasma level from the known $IC_{50}$ value. To demonstrate that the compound can be quantitatively extracted from plasma as active inhibitor, controls for each inhibitor include normal rat plasma, normal rat plasma spiked with compound, and buffer dilutions of compound. All control samples are subjected to acetonitrile precipitation and analyzed with the thiopeptolide assay.

Bioassay of Example 1

At a dose of 50 mg/kg peak plasma levels of 71 μM were achieved at 1 to 4 hours. At 24 hours postdose, plasma levels of 29 μM were achieved.

TABLE 2

| Example Number | $IC_{50}$ (μM) | | | | |
|---|---|---|---|---|---|
| | MMP1 | MMP-2CD | MMP 3CD | MMP-7 | MMP-13CD |
| A1 | >100 | 5.2 | 9.6 | >100 | 11.0 |
| A4 | >100 | 2.7 | 4.6 | >100 | 3.7 |
| A5 | >100 | 0.9 | 0.5 | 35.6 | 1.1 |
| A6 | >100 | 1.5 | 3.9 | >100 | 8.0 |
| A8 | >100 | 1.6 | 2.5 | >100 | 4.8 |
| A10 | >100 | 9.4 | 26.5 | >100 | 63.0 |
| A12 | >100 | 0.6 | 1.0 | 64.9 | 1.7 |
| A13 | >100 | 1.2 | 2.3 | >100 | 7.3 |
| A14 | >100 | 7.8 | 5.2 | >100 | 42.6 |
| A16 | >100 | 5.5 | 6.5 | >100 | 34.4 |
| A17 | >100 | 0.7 | 0.9 | 53.3 | 4.4 |
| A19 | >100 | 1.0 | 1.7 | 92.9 | 3.0 |
| A21 | >100 | 3.3 | 7.5 | >100 | 9.2 |
| A22 | >100 | 3.0 | 9.0 | >100 | 10.0 |
| A25 | >100 | 1.8 | 5.2 | >100 | 5.2 |
| A26 | >100 | 1.5 | 4.2 | >100 | 5.4 |
| A27 | >100 | 1.1 | 7.7 | >100 | 5.8 |
| A28 | >100 | 1.8 | 4.5 | >100 | 8.7 |
| A31 | >100 | 3.3 | 6.4 | >100 | 12.8 |
| A35 | >100 | 1.1 | 1.7 | >100 | 4.4 |
| A38 | >100 | 0.6 | 1.4 | >100 | 4.2 |

TABLE 3

| Example Number | IC$_{50}$ ($\mu$M) | | | | |
|---|---|---|---|---|---|
| | MMP1 | MMP-2CD | MMP 3CD | MMP-7 | MMP-13CD |
| B1 | >100 | 2.7 | 8.8 | >100 | 14.2 |
| B2 | >100 | 22.2 | 89.3 | >100 | >100 |
| B3 | >100 | 2.1 | 6.1 | 93.5 | 13.6 |
| B4 | >100 | 9.1 | 8.1 | >100 | 20.5 |
| B5 | >100 | 1.2 | 2.3 | >100 | 3.3 |
| B6 | >100 | 3.1 | 9.0 | >100 | 4.4 |
| B8 | >100 | 1.1 | 3.0 | >100 | 7.6 |
| B9 | >100 | 0.8 | 1.4 | 70.2 | 4.0 |
| B10 | >100 | 0.3 | 2.4 | >100 | 8.0 |

TABLE 4

| Example Number | IC$_{50}$ ($\mu$M) | | | | |
|---|---|---|---|---|---|
| | MMP1 | MMP-2CD | MMP 3CD | MMP-7 | MMP-13CD |
| C2 | >100 | 0.6 | 1.0 | 89 | 0.7 |
| C3 | >100 | 0.9 | 1.5 | 78.1 | 3.8 |
| C4 | >100 | 7.4 | 5.9 | >100 | 13.2 |
| C5 | >100 | 26.3 | 36.5 | >100 | 53.9 |
| C6 | >100 | 1.6 | 0.6 | 48.4 | 1.8 |

TABLE 5

| Example Number | IC$_{50}$ ($\mu$M) | | | | |
|---|---|---|---|---|---|
| | MMP1 | MMP-2CD | MMP 3CD | MMP-7 | MMP-13CD |
| D1 | >100 | 1.7 | 2.9 | >100 | 2.4 |
| D2 | >100 | 1.8 | 4.6 | >100 | 7.1 |
| D3 | >100 | 2.9 | 8.6 | >100 | 11.8 |
| D5 | >100 | 1.2 | 8.6 | >100 | 7.7 |
| D6 | >100 | 1.4 | 2.5 | 92.1 | 3.3 |
| D8 | >100 | 7.0 | 19.0 | >100 | 39 |
| D9 | >100 | 4.3 | 14.2 | >100 | 11.7 |
| D10 | >100 | 2.5 | 4.2 | >100 | 11.1 |

TABLE 6

| Example Number | IC$_{50}$ ($\mu$M) | | | | |
|---|---|---|---|---|---|
| | MMP1 | MMP-2CD | MMP 3CD | MMP-7 | MMP-13CD |
| E1 | >100 | 1.1 | 3.9 | >100 | 7.9 |
| E3 | >100 | 9.1 | 44.7 | >100 | 15.0 |
| E4 | >100 | 0.7 | 3.1 | >100 | 4.3 |

TABLE 7

| Example Number | IC$_{50}$ ($\mu$M) | | | | |
|---|---|---|---|---|---|
| | MMP1 | MMP-2CD | MMP 3CD | MMP-7 | MMP-13CD |
| F1 | >100 | 1.4 | 1.9 | 62.0 | 4.1 |
| F2 | >100 | 0.9 | 1.8 | 26.4 | 1.2 |
| F3 | >100 | 3.9 | 8.7 | >100 | 24.1 |
| F4 | 93.7 | 0.3 | 0.6 | 42.7 | 2.2 |
| F5 | >100 | 0.7 | 1.0 | 40.9 | 0.7 |
| F6 | 68.7 | 0.2 | 0.2 | 14.8 | 0.3 |
| F7 | 40.9 | 0.3 | 0.4 | 12.3 | 0.3 |
| F8 | 61.3 | 0.1 | 0.4 | 7.0 | 0.2 |
| F9 | >100 | 9.8 | 22.6 | >100 | 39.3 |
| F10 | >100 | 2.1 | 2.7 | 74.1 | 1.9 |
| F11 | >100 | 2.1 | 2.7 | >100 | 3.6 |
| F12 | >100 | 0.3 | 0.7 | 32.4 | 3.7 |
| F13 | >100 | 9.3 | 26.5 | >100 | 24.1 |

TABLE 7-continued

| Example Number | IC$_{50}$ ($\mu$M) | | | | |
|---|---|---|---|---|---|
| | MMP1 | MMP-2CD | MMP 3CD | MMP-7 | MMP-13CD |
| F14 | >100 | 0.4 | 1.4 | 57.6 | 2.4 |
| F15 | >100 | 0.3 | 1.8 | 36.9 | 0.6 |
| F16 | >100 | 0.4 | 1.1 | 22.1 | 1.0 |

TABLE 8

| Example Number | IC$_{50}$ ($\mu$M) | | | | |
|---|---|---|---|---|---|
| | MMP1 | MMP-2CD | MMP 3CD | MMP-7 | MMP-13CD |
| H1 | | 0.1 | 0.5 | 18 | |
| H2 | | 0.2 | 1.7 | 1.8 | |
| H3 | | 0.07 | 0.3 | 6.4 | |
| H4 | 30.5 | 0.04 | 0.2 | 8.3 | 0.06 |
| H5 | | 0.1 | 0.9 | 13 | |
| H6 | | 0.6 | 4.6 | 100 | |
| H7 | | 0.1 | 1.3 | 26 | |
| H8 | | 0.3 | 0.7 | 29 | |

What is claimed is:
1. The compounds:

6-[2-(4-Chloro-phenoxy)-2-methyl-propionylamino]-2-(dibenzofuran-2-sulfonylamino)-hexanoic acid;

2-(Dibenzofuran-2-sulfonylamino)-6-[2-(pyridin-4-ylsulfanyl)-acetylamino]-hexanoic acid;

2-(Dibenzofuran-2-sulfonylamino)-6-[2-(2,4-dichloro-phenoxy)-acetylamino]-hexanoic acid;

2-(Dibenzofuran-2-sulfonylamino)-6-[2-(2-trifluoromethyl-phenyl)-acetylamino]-hexanoic acid;

2-(Dibenzofuran-2-sulfonylamino)-6-(2-thiophen-2-yl-acetylamino)-hexanoic acid;

2-(Dibenzofuran-2-sulfonylamino)-6-(2-phenoxy-butyrylamino)-hexanoic acid;

2-(Dibenzofuran-2-sulfonylamino)-6-(phenylsulfanyl-acetylamino)-hexanoic acid;

2-(Dibenzofuran-2-sulfonylamino)-6-(2-phenoxy-acetylamino)-hexanoic acid;

2-(Dibenzofuran-2-sulfonylamino)-6-[2-(3,4-dimethoxy-phenyl)-acetylamino]-hexanoic acid;

6-[2-(4-tert-Butyl-phenoxy)-acetylamino]-2-(dibenzofuran-2-sulfonylamino)-hexanoic acid;

2-(Dibenzofuran-2-sulfonylamino)-6-[3-(3,4-dimethoxy-phenyl)-propionylamino]-hexanoic acid;

6-(2-(Cyclopent-1-enyl-acetylamino)-2-(dibenzofuran-2-sulfonylamino)-hexanoic acid;

2-(Dibenzofuran-2-sulfonylamino)-6-[2-(4-methoxy-phenoxy)-acetylamino]-hexanoic acid;

2-(Dibenzofuran-2-sulfonylamino)-6-[2-(naphthalen-1-yloxy)-acetylamino]-hexanoic acid;

2-(Dibenzofuran-2-sulfonylamino)-6-[2-(4-nitro-phenoxy)-acetylamino]-hexanoic acid;

6-[4-(4Chloro-3-methyl-phenoxy)-butyrylamino]-2-(dibenzofuran-2-sulfonylamino)-hexanoic acid;

2-(Dibenzofuran-2-sulfonylamino)-6-[3-(4-methoxy-phenyl)-propionylamino]-hexanoic acid;

2-(Dibenzofuran-2-sulfonylamino)-6-(2-pyridin-3-yl-acetylamino)-hexanoic acid;

6-(2-Benzo[1,3]dioxol-5-yl-acetylamino)-2-(dibenzofuran-2-sulfonylamino)-hexanoic acid;

2-(Dibenzofuran-2-sulfonylamino)-6-(2-pyridin-2-yl-acetylamino)-hexanoic acid;
2-(Dibenzofuran-2-sulfonylamino)-6-[4-(4-nitro-phenyl)-butyrylamino]-hexanoic acid;
2-(Dibenzofuran-2-sulfonylamino)-6-(3-pyridin-4-yl-propionylamino)-hexanoic acid;
2-(Dibenzofuran-2-sulfonylamino)-6-(2-phenylamino-acetylamino)-hexanoic acid;
2-(Dibenzofuran-2-sulfonylamino)-6-(2-indol-1-yl-acetylamino)-hexanoic acid;
2-(Dibenzofuran-2-sulfonylamino)-6-[3-(2-methoxy-phenyl)-propionylamino]-hexanoic acid;
2-(Dibenzofuran-2-sulfonylamino)-6-(4-phenyl-butyrylamino)-hexanoic acid;
2-(Dibenzofuran-2-sulfonylamino)-6-(3-p-tolyl-propionylamino)-hexanoic acid;
6-[3-(4-Chloro-phenyl)-propionylamino]-2-(dibenzofuran-2-sulfonylamino)-hexanoic acid;
6-[2-(2-Benzyloxy-phenyl)-acetylamino]-2-(dibenzofuran-2-sulfonylamino)-hexanoic acid;
2-(Dibenzofuran-2-sulfonylamino)-6-[2-naphthalen-2-yl-acetylamino)-hexanoic acid;
2-(Dibenzofuran-2-sulfonylamino)-6-(4-1H-indol-3-yl-butyrylamino)-hexanoic acid;
2-(Dibenzofuran-2-sulfonylamino)-6-(2-naphthalen-1-yl-acetylamino)-hexanoic acid;
6-[3-(4-Chloro-phenoxy)-propionylamino]-2-(dibenzofuran-2-2-sulfonylamino)-hexanoic acid;
2-(Dibenzofuran-2-sulfonylamino)-6-(6-phenyl-hexanoylamino)-hexanoic acid;
2-(Dibenzofuran-2-sulfonylamino)-6-[4-thiophen-2-yl-butyrylamino)-hexanoic acid;
2-(Dibenzofuran-2-sulfonylamino)-6-[3,3,3-triphenyl-propionylamino)-hexanoic acid;
2-(Dibenzofuran-2-sulfonylamino)-6-(3-diethylamino-propionylamino)-hexanoic acid;
2-(Dibenzofuran-2-sulfonylamino)-6-(1-phenyl-cyclopropane carbonylamino)-hexanoic acid;
6-(3-Benzo[1,3]dioxol-5-yl-propionylamino)-2-(dibenzofuran-2-sulfonylamino)-hexanoic acid;
6-[(Cyclopentyl-phenyl-acetyl)-amino]-2-(dibenzofuran-2-sulfonylamino)-hexanoic acid;
2-(Dibenzofuran-2-sulfonylamino)-6-[3-(4-methoxy-phenyl)-ureido]-hexanoic acid;
2-(Dibenzofuran-2-sulfonylamino)-6-[3-(3,4-dichloro-phenyl)-ureido]-hexanoic acid;
2-(Dibenzofuran-2-sulfonylamino)-6-(3-pyridin-3-yl-thioureido)-hexanoic acid;
6-(3-Benzhydryl-thioureido)-2-(dibenzofuran-2-sulfonylamino)-hexanoic acid;
6-(3-Benzyl-thioureido)-2-(dibenzofuran-2-sulfonylamino)-hexanoic acid;
6-(3-Adamantan-1-yl-thioureido)-2-(dibenzofuran-2-sulfonylamino)-hexanoic acid;
2-(Dibenzofuran-2-sulfonylamino)-6-(3-naphthalen-2-yl-thioureido)-hexanoic acid;
6-(3-Allyl-ureido)-2-(dibenzofuran-2-sulfonylamino)-hexanoic acid;
6-(3-Benzyl-ureido)-2-(dibenzofuran-2-sulfonylamino)-hexanoic acid;
2-(Dibenzofuran-2-sulfonylamino)-6-(3-phenyl-ureido)-hexanoic acid;
2-(Dibenzofuran-2-sulfonylamino)-6-(3-phenyl-acryloylamino)-hexanoic acid;
2-(Dibenzofuran-2-sulfonylamino)-6-phenylacetylamino-hexanoic acid;
2-(Dibenzofuran-2-sulfonylamino)-6-(3-phenyl-propionylamino)-hexanoic acid;
6-[2-(4-Chloro-phenoxy)-acetylamino]-2-(dibenzofuran-2-sulfonylamino)-hexanoic acid;
2-(Dibenzofuran-2-sulfonylamino)-6-[2-(2,4,6-triisopropyl-phenyl)-acetylamino]-hexanoic acid;
2-(Dibenzofuran-2-sulfonylamino)-6-(2-phenyl-butyrylamino)-hexanoic acid;
2-(Dibenzofuran-2-sulfonylamino)-6-(4fluoro-benzenesulfonylamino)-hexanoic acid;
2-(Dibenzofuran-2-sulfonylamino)-6-(4-methoxy-benzenesulfonylamino)-hexanoic acid;
6-(4-Bromo-benzenesulfonylamino)-2-(dibenzofuran-2-sulfonylamino)-hexanoic acid;
6-(2-Acetylaminothiazole-5-sulfonylamino)-2-(dibenzofuran-2-sulfonylamino)-hexanoic acid;
6-(4-Acetylamino-benzensulfonylamino)-2-(dibenzofuran-2-sulfonylamino)-hexanoic acid;
6-Benzenesulfonylamino-2-(dibenzofuran-2-sulfonylamino)-hexanoic acid;
6-(Butane-1-sulfonylamino)-2-(dibenzofuran-2-sulfonylamino)-hexanoic acid;
2-(Dibenzofuran-2-sulfonylamino)-6-(naphthalene-2-sulfonylamino)-hexanoic acid;
2-(Dibenzofuran-2-sulfonylamino)-6-(naphthalene-1-sulfonylamino)-hexanoic acid;
2-(Dibenzofuran-2-sulfonylamino)-6-(2-phenyl-ethenesulfonylamino)-hexanoic acid;
2-(Dibenzofuran-2-sulfonylamino)-6-isobutoxycarbonylamino-hexanoic acid;
2-(Dibenzofuran-2-sulfonylamino)-6-(9H-fluoren-9-ylmethoxycarbonylamino)-hexanoic acid;
6-(Adamantan-1-yloxycarbonylamino)-2-(dibenzofuran-2-sulfonylamino)-hexanoic acid;
6-Allyloxycarbonylamino-2-(dibenzofuran-2-sulfonylamino)-hexanoic acid;
2-(Dibenzofuran-2-sulfonylamino)-4-(2-pyridin-4-yl-ethylcarbamoyl)-butyric acid;
2-(Dibenzofuran-2-sulfonylamino)-4-(2-methyl-butylcarbamoyl)-butyric acid;
2-(Dibenzofuran-2-sulfonylamino)-4-(2-hydroxy-propylcarbamoyl)-butyric acid;
2-(Dibenzofuran-2-sulfonylamino)-4-(4-propyl-phenylcarbamoyl)-butyric acid;
2-(Dibenzofuran-2-sulfonylamino)-4-(2,2-diphenyl-ethylcarbamoyl)-butyric acid;
4-Cyclopropylcarbamoyl-2-(dibenzofuran-2-sulfonylamino)-butyric acid;
2-(Dibenzofuran-2-sulfonylamino)-4-[(thiophen-2-ylmethyl)-carbamoyl]-butyric acid;
2-(Dibenzofuran-2-sulfonylamino)-4-(1,3-dimethyl-butylcarbamoyl)-butyric acid;
2-(Dibenzofuran-2-sulfonylamino)-4-(2-dimethylamino-ethylcarbamoyl)-butyric acid;
4-Benzylcarbamoyl-2-(dibenzofuran-2-sulfonylamino)-butyric acid;
2-(Dibenzofuran-2-sulfonylamino)-4-(2-thiophen-2-yl-ethylcarbamoyl)-butyric acid;

4-(4-Chloro-phenylcarbamoyl)-2-(dibenzofuran-2-sulfonylamino)-butyric acid;

2-(Dibenzofuran-2-sulfonylamino)-4-(4-phenyl-butylcarbamoyl)-butyric acid;

2-(Dibenzofuran-2-sulfonylamino)-4-[2-(1-methyl-1H-pyrrol-2-yl)-ethylcarbamoyl]-butyric acid;

2-(Dibenzofuran-2-sulfonylamino)-4-(2-methoxy-benzylcarbamoyl)-butyric acid;

2-(Dibenzofuran-2-sulfonylamino)-4-(naphthalen-1-ylmethyl)-carbamoyl]-butyric acid;

2-(Dibenzofuran-2-sulfonylamino)-pentanedioic acid 1-tert-butyl ester;

2-(Dibenzofuran-2-sulfonylamino)-4-phenethylcarbamoyl-butyric acid;

2-Dibenzofuran-2-sulfonylamino-4-oxo-4-(4-propyl-phenyl)-butyric acid;

3-(4-tert-Butoxy-phenyl)-2-(dibenzofuran-2-sulfonylamino)-propionic acid;

3-Benzyloxy-2-(dibenzofuran-2-sulfonylamino)-propionic acid;

2-(Dibenzofuran-2-sulfonylamino)-5-(toluene-4-sulfonylamino)-pentanoic acid;

5-Benzyloxycarbonylamino-2-(dibenzofuran-2-sulfonylamino)-pentanoic acid;

2-(Dibenzofuran-2-sulfonylamino)-butyric acid;

3-tert-Butoxy-2-(dibenzofuran-2-sulfonylamino)-propionic acid;

(Dibenzofuran-2-sulfonylamino)-phenyl-acetic acid; and 2-(Dibenzofuran-2-sulfonylamino)-3-(4-fluorophenyl)-propionic acid.

\* \* \* \* \*

UNITED STATES PATENT AND TRADEMARK OFFICE
CERTIFICATE OF CORRECTION

PATENT NO. : 6,294,674 B1
DATED : September 25, 2001
INVENTOR(S) : Joseph A. Picard et al.

It is certified that error appears in the above-identified patent and that said Letters Patent is hereby corrected as shown below:

<u>Column 31,</u>
Line 3, "Dibenzothiophene" should read -- Dibenzofuran --.
Line 21, "Dibenzothiophene" should read -- Dibenzofuran --.

<u>Column 37,</u>
Line 30, "(dibenzofuran-2-2-sulfonylamino)" should read
-- (dibenzofuran-2-sulfonylamino) --

Signed and Sealed this

Eighth Day of October, 2002

Attest:

JAMES E. ROGAN
Attesting Officer *Director of the United States Patent and Trademark Office*